US009878965B2

(12) United States Patent
Spannhoff et al.

(10) Patent No.: US 9,878,965 B2
(45) Date of Patent: Jan. 30, 2018

(54) PROCESS FOR THE PREPARATION OF BUTADIENE

(71) Applicant: BASF SE, Ludwigshafen (DE)

(72) Inventors: Kirsten Spannhoff, Ludwigshafen (DE); Andrei-Nicolae Parvulescu, Heidelberg (DE); Armin Lange de Oliveira, Heidelberg (DE); Stefan Marx, Dirmstein (DE); Mathias Feyen, Hirschberg (DE); Ulrich Müller, Neustadt (DE); Ekkehard Schwab, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/897,379

(22) PCT Filed: Jun. 13, 2014

(86) PCT No.: PCT/EP2014/062391
§ 371 (c)(1),
(2) Date: Dec. 10, 2015

(87) PCT Pub. No.: WO2014/198901
PCT Pub. Date: Dec. 18, 2014

(65) Prior Publication Data
US 2016/0145171 A1 May 26, 2016

(30) Foreign Application Priority Data
Jun. 13, 2013 (EP) ..................................... 13171800

(51) Int. Cl.
| | | |
|---|---|---|
| *C07C 1/24* | (2006.01) | |
| *C07C 1/20* | (2006.01) | |
| *B01J 29/89* | (2006.01) | |
| *B01J 37/00* | (2006.01) | |
| *C01B 39/02* | (2006.01) | |
| *C01B 39/08* | (2006.01) | |
| *C01B 39/12* | (2006.01) | |
| *C07C 1/207* | (2006.01) | |

(52) U.S. Cl.
CPC ............... *C07C 1/20* (2013.01); *B01J 29/89* (2013.01); *B01J 37/0045* (2013.01); *C01B 39/026* (2013.01); *C01B 39/08* (2013.01); *C01B 39/085* (2013.01); *C01B 39/12* (2013.01); *C07C 1/2076* (2013.01); *B01J 2229/183* (2013.01); *B01J 2229/37* (2013.01); *B01J 2229/62* (2013.01); *C01P 2006/12* (2013.01); *C07C 2529/70* (2013.01); *C07C 2529/78* (2013.01); *C07C 2529/86* (2013.01); *C07C 2529/89* (2013.01)

(58) Field of Classification Search
CPC .................................. C07C 1/24; C07C 1/20
USPC ........................................ 585/603, 606, 609
See application file for complete search history.

(56) References Cited

U.S. PATENT DOCUMENTS

| | | | |
|---|---|---|---|
| 2,421,361 A | 5/1947 | Toussaint et al. | |
| 8,921,635 B2* | 12/2014 | Ordomskiy | ............... C07C 1/20 585/607 |
| 2005/0031535 A1* | 2/2005 | Mueller | .................. C01B 37/00 423/716 |
| 2014/0163243 A1* | 6/2014 | Parvulescu | ............. C01B 39/06 549/272 |

FOREIGN PATENT DOCUMENTS

| | | |
|---|---|---|
| GB | 331482 | 6/1930 |
| WO | WO-2012/015340 | 2/2012 |

OTHER PUBLICATIONS

PCT International Preliminary Report on Patentability in PCT/EP2014/062391, dated Oct. 6, 2015, 7 pages.
PCT International Written Opinion in PCT/EP2014/062391, dated Sep. 5, 2014, 5 pages.
PCT International Search Report in PCT/EP2014/062391, dated Sep. 5, 2014, 3pages.
Corson, B.B., et al., Butadiene From Ethyl Alcohol: Study of the Variables of Operation, *Industrial and Engineering Chemistry* vol. 41, No. 5 May 1949, 1012-1017.
Liu, Lin, et al., Synthesis, characterization, and catalytic properties of MWW zeolite with variable Si/Al ratios, *Microporous and Mesoporous Materials*, vol. 94, 2006, 304-312.
Jones, Matthew D., et al., Investigations into the conversion of ethanol into 1,3-butadiene, *Catalysis Science & Technology* vol. 1 2011, 267-272.
Koningsveld, H. van, et al., Zeolite Structure Determination from X-Ray Diffraction, *Molecular Sieves*, vol. 2 Springer-Verlag Berlin 1999, 1-29.

\* cited by examiner

*Primary Examiner* — Thuan D Dang
(74) *Attorney, Agent, or Firm* — Oblon, McClelland, Maier & Neustadt, L.L.P.

(57) ABSTRACT

The present invention relates to a gas-phase process for the preparation of butadiene comprising
(i) providing a gas stream G-1 comprising ethanol;
(ii) contacting the gas stream G-1 comprising ethanol with a catalyst, thereby obtaining a gas stream G-2 comprising butadiene,
wherein the catalyst comprises a zeolitic material having a framework structure comprising $YO_2$, Y standing for one or more tetravalent elements, wherein at least a portion of Y comprised in the framework structure is isomorphously substituted by one or more elements X, as well as to a zeolitic material having a framework structure comprising $YO_2$, Y standing for one or more tetravalent elements, wherein at least a portion of Y comprised in the framework structure is isomorphously substituted by one or more elements X, wherein the zeolitic material displays a specific X-ray powder diffraction pattern, and to its use.

30 Claims, 6 Drawing Sheets

PROCESS FOR THE PREPARATION OF BUTADIENE

CROSS-REFERENCE TO RELATED APPLICATIONS

This application is the National Stage entry of PCT/EP2014/062391, filed on Jun. 13, 2014, which claims priority to European Application Number 13171800.9, filed on Jun. 13, 2013, which is incorporated herein by reference in their entireties.

The present invention relates to gas-phase process for the preparation of butadiene using a catalyst comprising a zeolitic material having a framework structure comprising $YO_2$, wherein at least a portion of Y is isomorphously substituted by one or more elements X. The present invention further relates to a zeolitic material having a specific framework structure comprising $YO_2$, wherein at least a portion of Y is isomorphously substituted by one or more elements X, and to its use as a catalytically active material for the preparation of butadiene, preferably from a gas stream comprising ethanol and optionally acetaldehyde.

INTRODUCTION

Butadiene is widely used in the chemical industry, for example as monomer and/or comonomer for the polymerization of elastomers. Currently, butadiene is almost entirely produced as a by-product of ethylene stem cracking of naphtha or gas oil feedstock. Due to increasing prices of oil, alternative methods for producing butadiene are of major interest.

In GB 331482 a process for the preparation of butadiene is described, wherein ethanol is contacted with aluminum oxide mixed with zinc oxide. However this process leads to a low yield of butadiene of 18%.

In Ind. Eng. Chem. 41 (1949), pages 1012-1017, the preparation of butadiene by a two step process is described. In the first step ethanol is dehydrogenated to acetaldehyde. In the second step, the obtained acetaldehyde is mixed with ethanol and converted to butadiene by use of impregnated catalysts. By use of the most efficient catalyst which comprises 2.3 weight % tantalum oxide on amorphous silica, a selectivity of butadiene of up to 69% and a conversion of the starting material of 34% were achieved for 8 h on stream. However, due to the price of tantalum, the catalyst is relatively expensive.

Furthermore, U.S. Pat. No. 2,421,361 discloses a process for the preparation of butadiene which comprises passing an acyclic mono-olefinic aldehyde like crotonaldehyde or acetaldehyde and a monohydric alcohol like ethanol over a catalyst of the group of zirconium oxide, tantalum oxide, columbium oxide and combinations of these oxides with amorphous silica. By use of the catalyst containing 2 weight-% of zirconium oxide, a 47% single-pass yield of the butadiene fraction was obtained which contained about 93 weight-% butadiene.

In WO 2012/015340 A1 a process for the preparation of butadiene is disclosed by use of a solid catalyst containing metals chosen from the group of silver, gold or copper, and metal oxides, chosen from the group of magnesium, titanium, zirconium, tantalum or niobium oxide. However, only low conversion rates in the range of from 6 to 64% were achieved in this process, wherein these values were determined during only 3 h time on stream.

The use of a variety of silica impregnated bi- and trimetallic catalysts for the conversion of ethanol and a mixture of ethanol and acetaldehyde to butadiene is described in M. D. Jones et al., Catal. Sci. Technol. 1 (2011), 267-272. However, all catalysts tended to show a reduced conversion rate over a period of 3 h.

DETAILED DESCRIPTION

Thus, it was an object of the present invention to provide a process for the preparation of butadiene which does not exhibit the disadvantages of the methods according to the prior art and wherein a high conversion of the starting material as well as a high selectivity to butadiene is achieved. Furthermore, it was an object of the present invention to improve the long term activity of the catalyst used.

Surprisingly, it was found that by a gas-phase process for the preparation of butadiene in the presence of a catalyst comprising a zeolitic material having a framework structure comprising $YO_2$, Y standing for one or more tetravalent elements, wherein at least a portion of Y comprised in the framework structure is isomorphously substituted by one or more elements X, a high conversion of the starting material and at the same time also high selectivity towards butadiene is achieved. Further, it was surprisingly found that the catalysts used in the process of the present invention show an improved long time activity compared to the catalysts used in the prior art.

Therefore, the present invention relates to a gas-phase process for the preparation of butadiene comprising (i) providing a gas stream G-1 comprising ethanol;
(ii) contacting the gas stream G-1 comprising ethanol with a catalyst, thereby obtaining a gas stream G-2 comprising butadiene,
wherein the catalyst comprises a zeolitic material having a framework structure comprising $YO_2$, Y standing for one or more tetravalent elements, wherein at least a portion of Y comprised in the framework structure is isomorphously substituted by one or more elements X.

In the inventive process, a gas stream G-1 comprising ethanol is provided in step (i) and subsequently contacted with a catalyst in step (ii). According to a preferred embodiment of the present invention, the gas stream provided in step (i) additionally comprises acetaldehyde.

Concerning the gas stream G-1 provided in step (i), no particular restriction applies according to the present invention relative to the composition of the gas stream G-1 regarding ethanol and optional acetaldehyde contained therein, provided that after contacting the gas stream G-1 with a catalyst in step (ii), a gas stream G-2 comprising butadiene is obtained. Thus, in general, no specific restrictions exist concerning the molar ratio of ethanol to acetaldehyde in the gas stream G-1. According to a preferred embodiment of the present invention, the molar ratio of ethanol to acetaldehyde in the gas stream G-1 is in the range of from 1:1 to 6:1, preferably from 2:1 to 3.5:1, and more preferably from 2.5:1 to 2.9:1.

Concerning the composition of the gas stream G-1, prior to contacting with the catalyst, no specific restrictions exist regarding the amount of ethanol or the mixture of ethanol and acetaldehyde comprised in the gas stream G-1. Thus, according to a preferred embodiment of the present invention, 70 vol.-% or more, preferably 75 vol.-% or more, more preferably 80 vol.-% or more of the gas stream G-1 comprises ethanol or a mixture of ethanol and acetaldehyde. It is further preferred that prior to contacting with the catalyst, 85 vol.-% or more, preferably 90 vol.-% or more, more preferably 95 vol.-% or more of the gas stream G-1 comprises ethanol or of a mixture of ethanol and acetaldehyde. Therefore, according to a preferred embodiment of the present invention, 80 vol.-% or more of the gas stream G-1 comprises ethanol or of a mixture of ethanol and acetaldehyde, wherein preferably 90 vol.-% or more, more preferably 95 vol.-% or more of the gas stream G-1 comprises ethanol or of a mixture of ethanol and acetaldehyde.

According to the present invention, the gas stream G-1 comprising ethanol provided in step (i) is subsequently contacted with a catalyst in step (ii), wherein the catalyst comprises a zeolitic material having a framework structure comprising $YO_2$, Y standing for one or more tetravalent elements, wherein at least a portion of Y comprised in the framework structure is isomorphously substituted by one or more elements X. In general, no specific restrictions exist concerning the molar ratio Y:X in the framework structure, provided that the catalyst is able to obtain a gas stream G-2 comprising butadiene. According to a preferred embodiment of the present invention, the molar ratio of Y:X in the framework structure ranges from 10:1 to 150:1, preferably from 20:1 to 80:1, more preferably from 30:1 to 50:1. According to another preferred embodiment of the present invention, the molar ratio of Y:X in the framework structure ranges from 50:1 to 700:1, preferably from 100:1 to 600:1, more preferably from 170:1 to 520:1.

According to the present invention, X preferably stands for one or more trivalent, tetravalent, and/or pentavalent elements, wherein generally, there are no specific restrictions concerning the chemical nature of the one or more trivalent, tetravalent, and/or pentavalent elements. According to a preferred embodiment, X stands for one or more trivalent, tetravalent, and/or pentavalent elements, wherein the one or more elements X are preferably selected from the group consisting of Zr, Ti, Sn, Ga, Nb, Ta, Sc, Ge, Al, B, Fe and combinations of two or more thereof, more preferably selected from the group consisting of Zr, Ti, Sn, Ga, Ge, Ta, and combinations of two or more thereof, more preferably selected from the croup consisting of Zr, Ti, Sn, Ta, and combinations of two or more thereof, wherein even more preferably X stands for Zr and/or Ta.

Also no specific restrictions exist concerning the tetravalent element Y comprised in the framework structure of the zeolitic material. According to a preferred embodiment of the present invention, Y is selected from the group consisting of Si, Sn, Ti, Zr, Ge and combinations of two or more thereof, preferably selected from the group consisting of Si, Ti, Ge, and combinations of two or more thereof, and more preferably Y stands for Si.

As to the zeolitic material comprised in the catalyst, no specific restrictions exist. Said zeolitic material may be any suitable zeolitic material having an BEA, MWW, MFI, MEL, MOR, RUT, DOH, MTN, FER, FAU, CDO, LEV, CHA framework structure, provided that it may act as catalyst in the process for the preparation on butadiene. According to a preferred embodiment of the present invention, the catalyst comprises a zeolitic material having a framework structure selected from the group consisting of BEA, MWW, MFI, MEL, MOR, RUT, DOH, MTN, FER, FAU and combinations of two or more thereof, preferably selected from the group consisting of BEA, MWW, MFI, MEL and combinations of two or more thereof, and more preferably selected from BEA and MWW.

According to a preferred embodiment of the present invention, the catalyst used in step (ii) of the present invention comprises isomorphously substituted zeolite beta, wherein the framework structure of the zeolite beta comprises Si and wherein at least a portion of Si comprised in the framework structure of the zeolite beta is isomorphously substituted by one or more elements X, preferably selected from the group consisting of Zr, Ti, Sn, Ga, Ge, and combinations of two or more thereof, more preferably selected from the croup consisting of Zr, Ti, Sn, and combinations of two or more thereof, even more preferably X stands for Zr. Further, according to a preferred embodiment of the present invention, the catalyst used in step (ii) of the present invention comprises a zeolitic material having an MWW framework structure, wherein the framework comprises Si and wherein at least a portion of Si comprised in the framework structure of the zeolitic material is isomorphously substituted by one or more elements X, preferably selected from the group consisting of Zr, Ti, Sn, Ga, Ge, Ta, and combinations of two or more thereof, more preferably selected from the croup consisting of Zr, Ti, Sn, Ta, and combinations of two or more thereof, even more preferably X stands for Ti and/or Sn and/or Ta.

The notation "X-MWW" and "X-BEA" as used in the context of the present invention describes the isomorphously substituted zeolitic materials having an MWW and BEA framework structure, respectively, wherein X stands for the element by which the zeolitic material is isomorphously substituted.

Thus, according to a preferred embodiment of the present invention, the catalyst comprises isomorphously substituted zeolite beta preferably selected from the group consisting of Zr-BEA, Ti-BEA, Sn-BEA and combinations of two or more thereof, wherein more preferably the catalyst comprises Zr-BEA and/or an isomorphously substituted zeolitic material having an MWW framework structure preferably selected from the group consisting of Zr-MWW, Ti-MWW, Sn-MWW, Ta-MWW and combinations of two or more thereof, wherein more preferably the catalyst comprises Sn-MWW and/or Ta-MWW According to a particularly preferred embodiment of the present invention, the catalyst comprises isomorphously substituted zeolite beta and/or Sn-MWW and/or Ta-MWW, preferably Zr-BEA and/or Ta-MWW.

According to a preferred embodiment of the present invention, wherein the zeolitic material comprised in the catalyst has an MWW framework structure, the tetravalent element Y comprised in the MWW framework structure of the zeolitic material is selected from the group consisting of Si, Sn, Ti, Zr, Ge and combinations of two or more thereof, preferably selected from the group consisting of Si, Ti, Ge, and combinations of two or more thereof, more preferably Y stands for Si. Further, according to a particularly preferred embodiment of the present invention, wherein the zeolitic material comprised in the catalyst has an MWW framework structure, the one or more trivalent, tetravalent, and/or pentavalent element X by which the zeolitic material is isomorphously substituted, is selected from the group consisting of Zr, Ti, Sn, Ga, Nb, Ta, Sc, Ge, Al, B, Fe and combinations of two or more thereof, more preferably selected from the group consisting of Zr, Ti, Sn, Ga, Ge, Ta, and combinations of two or more thereof, more preferably selected from the croup consisting of Zr, Ti, Sn, Ta, and combinations of two or more thereof, even more preferably X stands for Sn and/or Ti and/or Ta. It is further preferred, that the zeolitic material comprised in the catalyst has an MWW framework structure, wherein the tetravalent element Y comprised in the MWW framework structure is preferably selected from the group consisting of Si, Ti, Ge, and combinations of two or more thereof, and preferably Y stands for Si, and wherein the one or more trivalent, tetravalent, and/or pentavalent element X by which the zeolitic material is isomorphously substituted, is preferably selected from the group consisting of Zr, Ti, Sn, Ta, and preferably X stands for Ti and/or Sn and/or Ta.

According to a particularly preferred embodiment of the present invention, the zeolitic material comprised in the catalyst has an MWW framework structure, wherein Y is Si and X is Ta.

According to a particularly preferred embodiment of the present invention, the zeolitic material comprised in the catalyst has an MWW framework structure, wherein Y is Si and X is Ti.

Concerning the zeolitic material comprised in the catalyst used in (ii), the zeolitic material may further comprise one or more non-framework elements. Concerning the method by which the one or more non-framework elements are disposed on the catalyst, no specific restrictions exist. Therefore, it may be conceivable to dispose the one or more non-framework elements on the catalyst by one or more ion-exchange procedures, wherein the term "ion-exchange" according to the present invention generally refers to non-framework ionic elements contained in the zeolitic material.

As regards the ion-exchange procedure, no particular restriction either regarding the specific ion-exchange method which is applied, nor with respect to whether said step is repeated and, if yes, the number of times said step is repeated. Thus, by way of example, ion-exchange may be conducted with the aid of a solvent or solvent mixture in which the ion to be exchanged is suitably dissolved. With respect to the type of solvent which may be used, there is again no particular restriction in this respect, provided that the ions to be exchanged may be solvated therein. Thus, by way of example, the solvent or mixture of solvents which may be used include water and alcohols, and in particular short chain alcohols selected among $C_1$-$C_4$, and preferably $C_1$-$C_3$ alcohols, in particular methanol, ethanol or propanol, including mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol such as water and methanol or water and ethanol or water and propanol or water and methanol and ethanol or water and methanol and propanol or water and ethanol and propanol or water and methanol and ethanol and propanol. According to a preferred embodiment of the present invention, however, water or a mixture of water and one or more alcohols is preferred, wherein a mixture of water and ethanol is further preferred, deionized water being particularly preferred as the solvent for the one or more ion-exchange procedures.

As regards the amount of the one or more solvents preferably used in the ion-exchange procedure in order to dispose the one or more non-framework elements on the catalyst, there is again no particular restriction, provided that the one or non-framework elements are effectively disposed on the catalyst. Thus, by way of example, an excess of solvent or solvent mixture may be used in the ion-exchange procedure wherein one or more solvated non-framework elements enter the porous system of the zeolitic material and, in counterpart, ions contained in the zeolitic material against which the one or more non-framework elements are exchanged are suitably solvated in the solvent or solvent mixture and accordingly allowed to exit the porous system of the zeolitic material. It is preferred that the ion-exchange procedure is conducted with an excess of solvent or solvent mixture, wherein, by way of example, a liquid to solid weight ratio ranging anywhere from 0.1 to 50 may be used. According to said preferred embodiments of the present invention, however, it is preferred that the liquid to solid weight ratio being the weight ratio of the solvent or solvent mixture to the zeolitic material, is comprised in the range of from 1 to 45, more preferably of from 5 to 43, more preferably of from 10 to 40, more preferably of from 20 to 38, and even more preferably of from 25 to 35. According to particularly preferred embodiments of the present invention, the liquid to solid weight ratio employed in the ion-exchange procedure is comprised in the range of from 27 to 33.

According to a preferred embodiment of the present invention, the one or more non-framework elements are disposed on the catalyst by impregnation, more preferably by ion-exchange.

According to a preferred embodiment of the present invention, the one or more non-framework elements comprised in the zeolitic material are selected from the group consisting of Zn, Zr, Sn, Ti, Co, Cu, Fe, and combinations of two or more thereof, preferably Zn, Zr, Sn, Ti, and combinations of two or more thereof, more preferably Zn, Zr, Sn, and combinations of two or more thereof, wherein even more preferably the non-framework element is Zn.

Thus, according to a preferred embodiment of the present invention, the zeolitic material further comprises Zn as non-framework element, wherein Zn is preferably disposed on the catalyst by impregnation, more preferably by ion-exchange.

Generally, there are no specific restrictions how the zeolitic material comprised in the catalyst which is used in step (ii) of the present invention is provided. In particular, any conceivable process for synthesizing such a zeolite can be employed for providing the zeolitic material. According to a preferred embodiment of the present invention, the zeolitic material comprised in the catalyst which is used in step (ii) is provided by a process comprising (a) providing a zeolitic material having a framework structure comprising $Z_2O_3$ and $YO_2$, wherein Y stands for one or more tetravalent elements and Z stands for a trivalent element;

(b) removing at least a portion of Z by treating the zeolitic material provided in (a) with a liquid solvent system having a pH in the range of from 5.5 to 8;

(c) isomorphously substituting at least a portion of Y comprised in the framework structure of the zeolitic material obtained from (b) by one or more elements X by a process comprising (c.1) preparing an aqueous synthesis mixture containing the zeolitic material obtained from (b), optionally a template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, and a X source;

(c.2) hydrothermally synthesizing a X-containing zeolitic material from the synthesis mixture obtained from (c.1) thereby obtaining a X-containing zeolitic material in its mother liquor;

(c.3) optionally separating the X-containing zeolitic material obtained from (c.2) from its mother liquor;

(d) treating the X-containing zeolitic material obtained from (c) with an aqueous solution having a pH of at most 5.

According to a preferred embodiment of the present invention, $YO_2$ and $Z_2O_3$ comprised in the framework structure of the zeolitic materials provided in step (a) are contained in the framework structure as framework-forming elements, as opposed to non-framework elements which can be present in the pores and cavities formed by the framework structure and which can be typical for zeolitic materials in general.

As far as the chemical nature of Z is concerned, no specific restrictions exist. In particular Z can be any conceivable trivalent element or mixture of two or more trivalent elements. Preferred trivalent elements according to the present invention include, but are not restricted to, Al, B, In, Ga and Fe. Preferably, Z is selected from the group consisting of Al, B, In, Ga, Fe and combinations of two or more thereof, Z preferably being B.

Also no specific restrictions exist concerning the one or more tetravalent element Y comprised in the framework structure of the zeolitic material provided in (a). According to a preferred embodiment of the present invention, Y is selected from the group consisting of Si, Sn, Ti, Zr, Ge and combinations of two or more thereof, preferably selected from the group consisting of Si, Ti, Ge, and combinations of two or more thereof, more preferably Y stands for Si.

Therefore, according to a particularly preferred embodiment of the present invention, Y stands for Si and Z stands for B.

According to preferred embodiments of the present invention, wherein Y stands for Si, any suitable silicon source may be used to provide the zeolitic material in (a), wherein preferably, the silicon source is a fumed silica, a mixture of two or more fumed silica, a colloidal silica such as ammonia-stabilized colloidal silica, a mixture of two or more colloidal silica, or a mixture of at least one fumed silica and at least one colloidal silica. Preferably, the silicon source comprises a colloidal silica, more preferably an ammonia-stabilized colloidal silica. More preferably, the silicon source is a colloidal silica, more preferably an ammonia-stabilized colloidal silica.

Further, according to preferred embodiments of the present invention, wherein Z stands for B, any suitable boron source may be used to provide the zeolitic material in (a), wherein preferably, the boron source is boric acid, a borate, in particular a water-soluble borate, a boron halide, boron oxide ($B_2O_3$), or a mixture of two or more thereof, with boric acid being especially preferred.

According to a particularly preferred embodiment of the present invention, wherein Z stands for B and Y stands for Si, and wherein the zeolitic material has an MWW framework structure, a MWW template compound is used in (a), wherein preferably, the MWW template compound is selected from the group consisting of selected from the group consisting of piperidine, hexamethylene imine, N,N,N',N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, N,N,N-trimethyl-1-adamantylammonium hydroxide, and a mixture of two or more thereof. More preferably, the MWW template compound is piperidine.

Concerning the treatment of the zeolitic material provided in (a) with a liquid solvent system having a pH in the range of from 5.5 to 8 according to (b) in order to remove at least a portion of Z, it is preferred, that the zeolitic material obtained from (b) is free of Z or essentially free of Z, i.e. contains Z only in traces as impurities.

Therefore, according to a particularly preferred embodiment of the present invention, wherein Z stands for B, zeolitic material obtained from (b) is free of B or essentially free of B, i.e. contains B only in traces as impurities.

Concerning the template compound used in (c.1), according to a preferred embodiment of the present invention, the used template compound is piperidine.

According to a preferred embodiment of the present invention, in (c) at least a portion of Y comprised in the framework structure of the zeolitic material is isomorphously substituted by one or more elements X, wherein X is preferably selected from the group consisting of Zr, Ti, Sn, Ga, Nb, Ta, Sc, Ge, Al, B, Fe and combinations of two or more thereof, more preferably selected from the group consisting of Zr, Ti, Sn, Ga, Ge, Ta, and combinations of two or more thereof, more preferably selected from the croup consisting of Zr, Ti, Sn, Ta, and combinations of two or more thereof.

According to a preferred embodiment of the present invention, wherein the zeolitic material comprised in the catalyst used in (ii) has an MWW framework structure, X stands for Ti and/or Sn, wherein the aqueous synthesis mixture prepared in (c.1) comprises a Ti source selected from the group consisting of tetrabutylorthotitanate, tetraisopropylorthotitanate, tetra-ethylorthotitanate, titanium dioxide, titanium tetrachloride, titanium tert-butoxide, and a mixture of two or more thereof, and/or a Sn source selected from the group consisting of $SnCl_4$, Sn(IV)-acetate, Sn(IV)-tert-butoxide, $SnBr_4$, $SnCl_4$, $SnF_4$, Sn(IV)-bisacetylacetonate dichloride, Sn(IV)-bisacetylacetonate dibromide, Sn(II)-acetate, Sn(II)acetylacetonate, Sn(II)-citrate, $SnCl_2$, $SnF_2$, $SnI_2$, $SnSO_4$, and mixtures of two or more thereof.

According to a particularly preferred embodiment of the present invention, wherein the zeolitic material comprised in the catalyst used in (ii) has an MWW framework structure, X stands for Ti and/or Sn, wherein the aqueous synthesis mixture prepared in (c.1) comprises tetrabutylorthotitanate as Ti source and/or Sn(IV)-tert-butoxide as Sn source.

As described above, the zeolitic material comprised in the catalyst may further comprise one or more non-framework elements. Thus, according to a preferred embodiment of the present invention the zeolitic material obtained from (d) is optionally subjected to impregnation with Zn, Zr, Sn, Ti, Co, Cu, Fe, and combinations of two or more thereof, preferably Zn, Zr, Sn, Ti, and combinations of two or more thereof, more preferably Zn, Zr, Sn, and combinations of two or more thereof, preferably impregnation is carried out by ion-exchange. According to a particularly preferred embodiment of the present invention, wherein the zeolitic material obtained from (d) is optionally subjected to impregnation with Zn, preferably impregnation is carried out by ion-exchange.

According to a particularly preferred embodiment of the present invention, the zeolitic material comprised in the catalyst used in (ii) having an MWW framework structure, in which at least a portion of Y comprised in the framework structure is isomorphously substituted by Ta, is provided by a process comprising (a) providing a zeolitic material having a framework structure comprising $Z_2O_3$ and $YO_2$, wherein Y stands for one or more tetravalent elements and Z stands for a trivalent element;

(b) removing at least a portion of Z by treating the zeolitic material provided in (a) with a liquid solvent system having a pH in the range of from 5.5 to 8;

(c) isomorphously substituting at least a portion of Y comprised in the framework structure of the zeolitic material obtained from (b) by Ta by incipient wetness.

The incipient wetness is conducted with the aid of a solvent or solvent mixture in which Ta is suitably dissolved. With respect to the type of solvent which may be used, there is no particular restriction Thus, by way of example, the solvent or mixture of solvents which may be used include water and alcohols, and in particular short chain alcohols selected among $C_1$-$C_4$, and preferably $C_1$-$C_3$ alcohols, in particular methanol, ethanol or propanol, including mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol such as water and methanol or water and ethanol or water and propanol or water and methanol and ethanol or water and methanol and propanol or water and ethanol and propanol or water and methanol and ethanol and propanol. According to a preferred embodiment of the present invention, however, water or a mixture of water and one or more alcohols is preferred, wherein a mixture of water and ethanol is further preferred, deionized water being particularly preferred.

According to a preferred embodiment of the present invention, incipient wetness is carried out by use of one or more inorganic or organic salts as Ta source. It is preferred according to the present invention that the one or more inorganic or organic salts are selected from the group consisting of halides, phosphates, hydroxides, carbonates, carboxylates, alcoholates, and combinations of two or more thereof, more preferably selected from the group consisting of chlorides, carboxylates, and combinations of two or more thereof, more preferably the ta source is ta oxalate.

According to a preferred embodiment of the present invention, wherein the zeolitic material comprised in the catalyst has a BEA framework structure comprising $X_2O_3$ and $YO_2$, wherein Y stands for one or more tetravalent elements and X stands for one or more trivalent, tetravalent, and/or pentavalent elements, the zeolitic material comprised in the catalyst which is used in step (ii) is preferably provided by a process comprising (a) preparing an aqueous synthesis mixture comprising a Y source, a X source, and optionally a template compound, preferably selected from the group consisting of piperidine, hexamethylene imine, N,N,N-trimethyl-1-adamantammonium hydroxide, piperidine, hexamethylene imine, dibenzyl-1,4-diazabicyclo[2,2,2]octane, dibenzylmethylammonium, tetraethylammonium hydroxide, and combinations of two or more thereof;

(b) optionally adding seed crystals and/or an acid to the mixture prepared in (e), wherein an aqueous HF solution is preferably used as the acid;

(c) hydrothermaly synthesizing a zeolitic material having a BEA framework structure comprising $X_2O_3$ and $YO_2$ from the aqueous synthesis mixture prepared in (e), optionally after step (f), wherein Y stands for one or more tetravalent elements and X stands for one or more trivalent, tetravalent, and/or pentavalent elements.

According to a preferred embodiment of the present invention, wherein the zeolitic material comprised in the catalyst used in (ii) has a BEA framework structure, X stands for one or more trivalent, tetravalent, and/or pentavalent elements preferably selected from the group consisting of Zr, Ti, Sn, Ga, Nb, Ta, Sc, Ge, Al, B, Fe and combinations of two or more thereof, more preferably selected from the group consisting of Zr, Ti, Sn, Ga, Ge, and combinations of two or more thereof, more preferably selected from the croup consisting of Zr, Ti, Sn, and combinations of two or more thereof, even more preferably X stands for Zr, and Y stands for one or more tetravalent elements preferably selected from the group consisting of Si, Sn, Ti, Zr, Ge and combinations of two or more thereof, more preferably selected from the group consisting of Si, Ti, Ge, and combinations of two or more thereof, more preferably Y stands for Si.

According to a preferred embodiment of the present invention, wherein Y stands for Si, any suitable silicon source may be used to prepare the aqueous synthesis mixture in (a), wherein preferably, the silicon source is selected from the group consisting of tetraethylorthosilicate, a fumed silica, a colloidal silica such as ammonia-stabilized colloidal silica, and combinations of two or more thereof, more preferably, the silicon source is tetraethylorthosilicate.

According to a preferred embodiment of the present invention, wherein X stands for Zr, any suitable Zr source may be used to prepare the aqueous synthesis mixture in (a), wherein preferably, the Zr-source is selected from the group consisting of zirconium and zirconyl salts, more preferably from the group consisting of zirconium and zirconyl halides, zirconium hydroxide, zirconyl nitrate, zirconium alkoxides, and mixtures of two or more thereof, more preferably from the group consisting of zirconium and zirconyl bromide, chloride, fluoride, zirconyl nitrate, C1-C4 alkoxides of Zr, and mixtures of two or more thereof, more preferably from the group consisting of zirconium and zirconyl chloride, fluoride, zirconyl nitrate, C2-C3 alkoxides of Zr, and mixtures of two or more thereof, more preferably from the group consisting of zirconium and zirconyl chloride, zirconyl nitrate, C3 alkoxides of Zr, and mixtures of two or more thereof, more preferably from the group consisting of zirconyl chloride, zirconyl nitrate, Zn-n-propoxide, and mixtures of two or more thereof, wherein more preferably the Zr source is Zr-n-propoxide.

Therefore, according to a particularly preferred embodiment of the present invention, wherein Y stands for Si and X stands for Zr, the aqueous synthesis mixture prepared in (a) comprises tetraethylorthosilicate as Si source and Zr-n-propoxide as Zr source.

According to a preferred embodiment of the present invention, wherein the aqueous synthesis mixture prepared in (a) comprises tetraethylorthosilicate and Zr-n-propoxide, the aqueous synthesis mixture prepared in (a) is heated at a temperature in the range of from 50 to 120° C., preferably from 85 to 100° C. prior to optionally adding seed crystals and/or an acid and preferably an aqueous HF solution to the mixture prepared in (a) according to (b) and prior to hydrothermally synthesizing a zeolitic material having a BEA framework structure comprising $X_2O_3$ and $YO_2$ from the aqueous synthesis mixture prepared in (a) according to (c) for removing one or more alcohols and in particular propanol and/or ethanol, and preferably for removing ethanol from the synthesis mixture by distillation.

As regards the particular conditions under which the gas stream G-1 is contacted with a catalyst according to the present invention in step (ii), no particular restrictions exist provided that a gas stream G-2 comprising butadiene is obtained. This, for example, applies to the temperature at which the contacting in step (ii) takes place. Accordingly, said contacting of the gas stream in step (ii) may be conducted according to the inventive process at a temperature in the range of from 200 to 600° C., preferably from 250 to 550° C., more preferably from 300 to 500° C., more preferably from 325 to 425° C., more preferably from 350 to 400° C. According to a particularly preferred embodiment of the present invention, contacting the gas stream G-1 with the catalyst is carried out at a temperature in the range of from 300 to 500° C., preferably from 325 to 425° C., more preferably from 350 to 400° C.

Same applies accordingly to the pressure under which the gas stream G-1 is contacted with a catalyst according to the present invention in step (ii) of the inventive process. Thus, in principle, said contacting may be conducted at any conceivable pressure, provided that a gas stream G-2 comprising butadiene is obtained. According to a preferred embodiment of the present invention, contacting the gas stream G-1 with the catalyst is carried out at a pressure in the range of from 1 to 5 bar, preferably from 1 to 2 bar.

According to a particularly preferred embodiment of the present invention, the gas stream G-1 is contacted with a catalyst according to the present invention in step (ii) at a temperature in the range of from 300 to 500° C., preferably from 325 to 425° C., more preferably from 350 to 400° C. at a pressure in the range of from 1 to 5 bar, preferably from 1 to 2 bar.

Furthermore, no particular restriction applies relative to the manner in which the inventive process for the preparation of butadiene is conducted, such that both a non-continuous mode as well as a continuous mode may be applied to the inventive process, wherein the non-continuous process may for example be conducted as a batch-process.

According to a preferred embodiment of the present invention, contacting gas stream G-1 with the catalyst is carried out in continuous mode. No specific restrictions exist concerning the set-up of the continuous process. Preferred continuous process set-ups include the use of one or more fixed-bed reactor. Thus, according to an preferred embodiment of the present invention, contacting the gas stream G-1 with the catalyst is carried out in one ore more reactors, wherein the one ore more reactors contain the catalyst in the form of a fixed bed.

As regards the preferred embodiments of the inventive process, wherein contacting the gas stream G-1 with the catalyst in step (ii) is performed in a continuous mode, in principle no restrictions apply relative to the liquid hourly space velocity (LHSV) at which the process is conducted, provided that a gas stream G-2 comprising butadiene is obtained. Accordingly, liquid hourly space velocities may be chosen for the contacting in step (ii) which lie in the range of from 0.1 to 30 $h^{-1}$, wherein preferably liquid hourly space velocities of from 0.2 to 15 $h^{-1}$ are chosen, more preferably of from 0.3 to 5 $h^{-1}$, more preferably of from 0.4 to 1 $h^{-1}$, and more preferably of from 0.5 to 0.7 $h^{-1}$. According to a particularly preferred embodiment of the inventive process, wherein contacting the gas stream G-1 with the catalyst in step (ii) is performed in a continuous mode, liquid hourly space velocities ranging from 0.5 to 0.7 $h^{-1}$ are chosen for the contacting of the gas stream in step (ii) with a catalyst according to the present invention.

Further, according to the present invention, it is preferred that prior to contacting the gas stream G-1 with the catalyst, the gas stream is heated. According to a preferred embodiment, the heating of the gas stream G-1 prior to contacting with the catalyst may be conducted at a temperature in the range of from 50 to 300° C., preferably from 100 to 250° C., and more preferably from 120 to 180° C. Thus, according to a preferred embodiment of the present invention, prior to contacting the gas stream G-1 with the catalyst, the gas stream G-1 is heated, preferably to a temperature in the range of from 100 to 250° C., more preferably from 120 to 180° C.

Further, according to a preferred embodiment of the present invention an activation of the catalyst takes place prior to contacting the gas stream G-1 with the catalyst, wherein, for example, the activation may be conducted by heating of the catalyst. Thus, according to a preferred embodiment of the present invention, prior to contacting the gas stream G-1 with the catalyst, the catalyst is activated, preferably by heating.

As regards the specific conditions under which the catalyst is activated, no particular restrictions exist, provided that by use of the activated catalyst a gas stream G-2 is obtained. Accordingly, said activation of the catalyst prior to contacting with the gas stream G-1 may be conducted according a preferred embodiment of the inventive process at a temperature in the range of from 200 to 550° C., preferably from 250 to 500° C., more preferably from 300 to 450° C., more preferably from 325 to 425° C., more preferably from 350 to 400° C. The same applies to the duration of the activation. Thus, according to a preferred embodiment of the present invention, the activation prior to contacting with the gas stream G-1 is conducted for a period in the range of from 5 to 120 min, more preferably from 10 to 60 min, more preferably from 20 to 40 min. Thus, according to a preferred embodiment of the present invention, it is preferred that the catalyst is activated by heating to a temperature in the range of from 300 to 450° C., preferably from 325 to 425° C., more preferably from 350 to 400° C., preferably for a period in the range of from 5 to 120 min, more preferably from 10 to 60 min, more preferably from 20 to 40 min.

According to a preferred embodiment of the present invention, a heating ramp is used for reaching the temperature of activation, wherein the heating rate preferably ranges from 0.5 to 10 K/min, preferably 1 to 5 K/min, preferably from 1 to 3 K/min. Thus, according to a preferred embodiment of the present invention, the catalyst is heated with a temperature ramp in the range of from 0.5 to 10 K/min, preferably 1 to 5 K/min, preferably from 1 to 3 K/min.

Generally, no specific restrictions exist concerning the set-up in which the activation is conducted. According to a particularly preferred embodiment of the present invention, the catalyst is activated in the one or more reactors.

It is preferred that during heating the catalyst is flushed with an inert gas. As to the chemical nature of the inert gas, no particular restrictions exist. According to a particularly preferred embodiment of the present invention that during heating the catalyst is flushed with an inert gas, preferably with an inert gas selected from the group consisting of helium, nitrogen, argon, and mixtures of two or more thereof, wherein the inert gas is more preferably nitrogen.

As to the amount of butadiene comprised in the gas stream G-2 obtained from the contacting of the gas stream G-1 with the catalyst in step (ii) of the present invention, no particular restrictions exist. However, it was surprisingly found that by a process for the preparation of butadiene according to the inventive process, a gas stream G-2 is obtained containing butadiene in an amount of from 10 to 90 vol-%, preferably from 20 to 80 vol-%, more preferably from 30 to 70 vol-%, based on the total volume of the gas stream G-2. Therefore, embodiments of the present invention are preferred wherein the gas stream G-2 contains butadiene in an amount of from 10 to 90 vol-%, preferably from 20 to 80 vol-%, more preferably from 30 to 70 vol-%, based on the total volume of the gas stream G-2.

According to preferred embodiments of the present invention, the process for the preparation of butadiene further comprises a separation of butadiene from the gas stream G-2 obtained from step (ii) of the present invention, wherein a purified gas stream G-3 comprising butadiene is obtained. Generally, there are no restrictions concerning the method for the separation of butadiene from the gas stream G-2, provided that a purified gas stream G-3 comprising butadiene is obtained. Such methods may include thermal separation. Preferably, the separation of butadiene from the gas stream G-2 is achieved by thermal separation, more preferably by distillation.

Thus, embodiments of the present invention are preferred, wherein the process for the preparation of butadiene further comprises (iii) separating butadiene from the gas stream G-2, thereby obtaining a purified gas stream G-3 comprising butadiene, wherein the separation is preferably achieved by thermal separation, more preferably by distillation.

According to a preferred embodiment of the present invention, the gas stream G-2 comprising butadiene obtained from step (ii) of the present invention may comprise further compounds resulting from contacting the gas stream G-1 with the catalyst. Thus, according to preferred embodiments of the invention the gas stream G-2 comprising butadiene further comprises diethyl ether. If the gas stream G-2 comprising butadiene further comprises diethyl ether, it is preferred that the diethyl ether is separated from the gas stream G-2 comprising butadiene. It is further preferred that the separation is carried out by thermal separation, preferably by distillation.

Further, it was found that the separated diethyl ether may be recycled to the gas-phase process for the preparation of butadiene according to the present invention, wherein it is preferred to recycle the separated diethyl ether as a component of the gas stream G-1 which is contacted with a catalyst in step (ii). Therefore, according to a preferred embodiment of the present invention, the separated diethyl ether is recycled to the gas-phase process for the preparation of butadiene according to the present invention, wherein the separated diethyl ether is preferably recycled as a component of the gas stream G-1 which is contacted with the catalyst in step (ii) to obtain butadiene. Thus, according to a preferred embodiment of the present invention, the gas stream G-2 further comprises diethyl ether, and wherein the diethyl ether is separated from the gas stream G-2, preferably by thermal separation, more preferably by distillation, and recycling the separated diethyl ether to the gas-phase process for the preparation of butadiene, preferably as component of the gas stream G-1.

According to preferred embodiments of the present invention, wherein G-2 further comprises diethyl ether which is preferably separated from G-2 and recycled preferably as component of the gas stream G-1, it is preferred that the gas stream G-2 prior to separating the diethyl ether contains diethyl ether in an amount of from 1 to 65 vol-%, preferably from 1 to 35 vol-%, more preferably from 2 to 20 vol-%, based on the total volume of the gas stream G-2. Thus, according to a particularly preferred embodiment of the present invention, the gas stream G-2 contains the diethyl ether in an amount of from 1 to 65 vol-%, preferably from 1 to 35 vol-%, more preferably from 2-20 vol-%, based on the total volume of the gas stream G-2.

As regards the separated diethyl ether from the gas stream G-1, according to a preferred embodiment of the present invention, at least a portion of the separated diethyl ether is hydrolyzed to ethanol prior to its recycling to the gas-phase process for the preparation of butadiene, preferably as component of the gas stream G-1. Thus, according to a preferred embodiment of the present invention, the process for the preparation of butadiene further comprising hydrolyzing at least a portion of the separated diethyl ether to ethanol prior to its recycling to the gas-phase process for the preparation of butadiene, preferably as component of the gas stream G-1.

As to the conditions under which hydrolyzation is conducted, according to a preferred embodiment of the present invention, the separated diethyl ether is hydrolyzed under acidic conditions, more preferably in the presence of a solid catalyst.

According to a preferred embodiment of the present invention, wherein the gas stream G-2 further comprises diethyl ether, the gas stream G-2 may further comprise crotonaldehyde. Thus, according to a preferred embodiment of the present invention, the gas mixture G-2 further comprises crotonaldehyde.

According to a preferred embodiment of the embodiment of the present invention, wherein the gas stream G-2 further comprises crotonaldehyde, it is preferred that the gas stream G-2 contains the crotonaldehyde in an amount of from 0.1 to 15 vol-%, preferably from 0.5 to 10 vol-%, more preferably from 1 to 5 vol-%, based on the total volume of the gas stream G-2.

According to a particularly preferred embodiment of the present invention, the gas stream G-2 comprising butadiene is free of crotonaldehyde or essentially free of crotonaldehyde, i.e. contains crotonaldehyde only in traces.

According to a preferred embodiment of the present invention, the catalyst is subjected to regeneration, wherein regeneration may be conducted by any suitable method. Conceivable methods are, for example to regenerate the catalyst by thermal treatment, preferably in the presence of oxygen. Further, there are no particular restrictions concerning the temperature under which the regeneration is conducted. According to a preferred embodiment of the present invention, the thermal treatment is conducted, for example, at a temperature in the range of from 200 to 600° C., preferably from 300 to 550° C., more preferably from 400 to 500° C. Therefore, according to a preferred embodiment of the present invention the process for the preparation of butadiene according to the present invention further comprises regenerating the catalyst, preferably by thermal treatment in the presence of oxygen, wherein the thermal treatment is preferably performed at a temperature in the range of from 100 to 700° C., preferably from 350 to 600° C., more preferably from 450 to 570° C.

According to a particularly preferred embodiment of the present invention, the catalyst contacted with the gas stream G-1 in step (ii) comprises a zeolitic material according to any of the particular and preferred embodiments of the present invention as defined below.

Thus, surprisingly, it was found that by using a catalyst comprising a zeolitic material, having a framework structure comprising $YO_2$, Y standing for one or more tetravalent elements, wherein at least a portion of Y comprised in the framework structure is isomorphously substituted by one or more elements X, and wherein the zeolitic material has an X-ray powder diffraction pattern comprising at least the following reflections:

| Intensity (%) | Diffraction angle 2θ/° [Cu K(alpha 1)] |
|---|---|
| 67.0-87.0 | 15.16 ± 0.3 |
| 79.8-99.8 | 15.82 ± 0.3 |
| 45.3-65.3 | 22.47 ± 0.3 |
| 100 | 23.88 ± 0.3 |
| 52.3-72.3 | 27.06 ± 0.3 |
| 75.0-95.0 | 27.21 ± 0.3 | wherein 100% relates to the intensity of the maximum peak in the X-ray powder diffraction pattern in the process of the present invention, an unexpectedly high conversion of ethanol or of a mixture of ethanol and acetaldehyde may be achieved, wherein at the same time also a surprisingly high selectivity towards butadiene was achieved.

Therefore, in addition to relating to a process for the preparation of butadiene by use of a catalyst comprising a zeolitic material, the present invention also relates to a zeolitic material having a framework structure comprising $YO_2$, Y standing for one or more tetravalent elements, wherein at least a portion of Y comprised in the framework structure is isomorphously substituted by one or more elements X, and wherein the zeolitic material has an X-ray powder diffraction pattern comprising at least the following reflections:

| Intensity (%) | Diffraction angle 2θ/° [Cu K(alpha 1)] |
|---|---|
| 67.0-87.0 | 15.16 ± 0.3 |
| 79.8-99.8 | 15.82 ± 0.3 |
| 45.3-65.3 | 22.47 ± 0.3 |
| 100 | 23.88 ± 0.3 |
| 52.3-72.3 | 27.06 ± 0.3 |
| 75.0-95.0 | 27.21 ± 0.3 | wherein 100% relates to the intensity of the maximum peak in the X-ray powder diffraction pattern.

As far as the molar ratio Y:X in the framework structure of the zeolitic material is concerned, no particular restrictions exist, provided that at least a portion of Y is isomorphously substituted by one or more elements X. According to a preferred embodiment of the present invention, the molar ratio of Y:X in the framework structure ranges from 100:1 to 700:1, preferably from 300:1 to 600:1, more preferably from 450:1 to 550:1.

As mentioned above, X stands for one or more trivalent, tetravalent, and/or pentavalent elements, wherein generally, there are no specific restrictions concerning the chemical nature of the one or more trivalent, tetravalent, and/or pentavalent elements. According to a particularly preferred embodiment of the present invention, X stands for one or more trivalent, tetravalent, and/or pentavalent elements, preferably selected from the group consisting of Zr, Ti, Sn, Ga, Nb, Ta, Sc, Ge, Al, B, Fe and combinations of two or more thereof, more preferably selected from the group consisting of Zr, Ti, Sn, Ga, Ge, Ta, and combinations of two or more thereof, more preferably selected from the croup consisting of Zr, Ti, Sn, Ta, and combinations of two or more thereof, even more preferably X stands for Zr.

Also no specific restrictions exist concerning the tetravalent element Y comprised in the framework structure of the zeolitic material. According to a preferred embodiment of the present invention, Y is selected from the group consisting of Si, Sn, Ti, Zr, Ge and combinations of two or more thereof, preferably selected from the group consisting of Si, Ti, Ge, and combinations of two or more thereof, wherein more preferably Y stands for Si.

Therefore, according to a particularly preferred embodiment of the present invention, X stands for Zr and Y stands for Si.

Furthermore, there is no particular restriction according to the present invention as to the suitable physical and/or chemical characteristics of the inventive zeolitic materials. Thus, as regards, for example, the porosity and/or surface area of the inventive materials, these may adopt any conceivable values. In particular, as regards the BET surface area of the zeolitic materials as determined according to DIN 66131, it may accordingly range anywhere from 20 to 600 m²/g, more preferably in the range of from 30 to 500 m²/g.

According to a particularly preferred embodiment of the present invention, zeolitic material has a BET specific surface area of at least 20 m²/g, and preferably a BET specific surface area in the range of from 20 to 600 m²/g, more preferably in the range of from 30 to 500 m²/g, wherein the specific surface area as determined according to DIN 66131.

Generally, there are no specific restrictions how the zeolitic material as defined above is provided. Any conceivable process for synthesizing such a zeolite can be employed for providing the zeolitic material.

According to a particularly preferred embodiment of the present invention, wherein the Y is Si an X is Zr, the above defined zeolitic material is preferably provided by a process comprising
(a) providing a boron-containing zeolitic material having an MWW framework structure comprising $SiO_2$ and $B_2O_3$ (B-MWW);
(b) deboronating the B-MWW by treating the B-MWW provided in (a) with an aqueous solution;
(c) isomorphously substituting at least a portion of Si by Zr by a process comprising
  (c.1) preparing an aqueous synthesis mixture containing the deboronated B-MWW obtained from (b), an template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, and a Zr source;
  (c.2) hydrothermally synthesizing a Zr-containing zeolitic material from the synthesis mixture obtained from (c.1) thereby obtaining a Zr-containing zeolitic in its mother liquor;
  (c.3) separating the Zr-containing zeolitic material obtained from (c.2) from its mother liquor;
(d) treating the Zr-containing zeolitic material obtained from (c) with an aqueous solution having a pH of at most 5.

Generally, there are no specific restrictions how the B-MWW is provided in (a). Any conceivable process for synthesizing such a zeolite can be employed for providing the zeolitic material. Preferably, the zeolitic material is provided in (a) by a process including hydrothermally synthesizing the zeolitic material starting from suitable sources of $B_2O_3$ and $SiO_2$ in the presence of a suitable template compound, also referred to as structure directing agent.

According to a preferred embodiment of the present invention, the B-MWW is provided by a process comprising
(a.1) hydrothermally synthesizing a B-MWW precursor from an aqueous synthesis mixture containing a silicon source, a boron source, and an MWW template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyl-trimethylammonium hydroxide, and a mixture of two or more thereof, to obtain the B-MWW precursor in its mother liquor;
(a.2) separating the B-MWW precursor from its mother liquor, and calcining the separated B-MWW precursor, obtaining a B-MWW.

As far as the silicon source used in (a.1) is concerned, no specific restrictions exist. Preferably, the silicon source is a fumed silica or a colloidal silica such as ammonia-stabilized colloidal silica, with ammonia-stabilized colloidal silica being especially preferred.

As far as the boron source used in (a.1) is concerned, no specific restrictions exist. Preferably, the boron source is boric acid, a borate, in particular a water-soluble borate, a boron halide, boron oxide ($B_2O_3$), with boric acid being especially preferred.

As far as the MWW template compound used in (a.1) is concerned, no specific restrictions exist provided that the B-MWW precursor is obtained. Preferably, the MWW template compound is selected from the group consisting of selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, N,N,N-trimethyl-1-adamantylammonium hydroxide, and a mixture of two or more thereof. More preferably, the MWW template compound is piperidine.

According to a particularly preferred embodiment of the present invention, the aqueous synthesis mixture according to (a.1) comprises ammonia-stabilized colloidal silica, boric acid and piperidine.

According to a preferred embodiment of the present invention, the aqueous synthesis mixture is preferably subjected to a hydrothermal synthesis according to (a.1), wherein the zeolitic material is crystallized during the hydrothermal synthesis. During hydrothermal synthesis, the crystallization mixture may be stirred. The stirring rates as such can be suitably chosen depending, for example, on the volume of the aqueous synthesis mixture, the amount of the starting materials employed, the desired temperature, and the like. For example, the stirring rate is in the range of from 50 to 300 r.p.m. (rounds per minute), such as from 100 to 250 r.p.m. or from 130 to 170 r.p.m. Preferably, the crystallization time is in the range of from 3 to 8 days, more preferably from 4 to 6 days.

The temperature applied during the hydrothermal synthesis in (a.1) is preferably in the range of from 140 to 200° C., more preferably from 150° C. to 190° C., more preferably from 160 to 180° C., more preferably from 160 to less than 180° C., more preferably from 170 to 177° C.

After hydrothermal synthesis, the obtained B-MWW precursor is preferably suitably separated from its mother liquor according to (a.2). All conceivable methods of separating a B-MWW from its mother liquor are possible. These methods include, for example, filtration, ultrafiltration, diafiltration and centrifugation methods or, for instance, spray drying processes and spray granulation processes. A combination of two or more of these methods can be applied.

According to a preferred embodiment of the present invention, the B-MWW precursor is separated from its mother liquor by filtration, and the thus obtained material, for example in the form of a filter cake, is preferably subjected to washing with at least one suitable washing agent, preferably to washing with water After separation of the B-MWW precursor from the mother liquor, preferably by filtration, and preferably after washing, the washed B-MWW precursor is subjected to drying preferably at a temperature in the range of from 50 to 200° C., more preferably from 70 to 150° C., more preferably from 90 to 110° C.

After drying, the B-MWW precursor is subjected to calcination to obtain the B-MWW. During calcination, the MWW template compound is preferably at least partially, more preferably essentially completely removed from the framework structure. Preferred calcination temperatures are in the range of from 500 to 700° C., more preferably from 550 to 675° C., more preferably from 600 to 650° C. Preferred atmospheres under which the calcination is carried out include technical nitrogen, air, or lean air. Preferred calcination times are in the range of from 1 to 24 h, preferably from 5 to 20 h, more preferably from 8 to 18 h.

The B-MWW obtained from (a) is subjected to deboronation in (b) by a treatment with an aqueous solution. According to a preferred embodiment of the present invention, the aqueous solution has a pH of at most 7, preferably in the range of from 0 to 7, more preferably from 0 to 5, more preferably from 0 to 4, more preferably from 0 to 3, more preferably from 0 to 2.

The pH of the aqueous solution used in (b) is adjusted by a suitable amount of at least one acid which is dissolved in water. Generally, it is conceivable that in addition to the at least one acid, the aqueous solution contains at least one base, provided that the aqueous solution has a pH as defined above. Preferably, the aqueous solution used in (b) comprises water and at least one acid dissolved in the water.

According to a preferred embodiment of the present invention, the aqueous solution used in (b) comprises at least one organic acid or at least one inorganic acid or a mixture of at least one organic and at least one inorganic acid. In principle, any conceivable acid may be comprised in the aqueous solution used in (b). Preferably, the organic acid is selected from the group consisting of oxalic acid, acetic acid, citric acid, methane sulfonic acid, and a mixture of two or more thereof. Preferably, the inorganic acid is selected from the group consisting of phosphoric acid, sulphuric acid, hydrochloric acid, nitric acid, and a mixture of two or more thereof. Preferably, at least one inorganic acid is used. Preferably, the inorganic acid is nitric acid.

In general, there is no particular restriction as to the concentration of the organic and the inorganic acid comprised in the aqueous solution used in (b), provided the pH of the aqueous solution used in (b) is as defined above.

Preferably, the zeolitic material is treated in (b) with the aqueous solution at a temperature in the range of from 20° C. to 200° C., more preferably from 40° C. to 160° C., more preferably from 60° C. to 140° C., more preferably from 80° C. to 120° C.

Preferably, the zeolitic material is treated in (b) with the aqueous solution for a period in the range of from 1 min to 50 h, more preferably from 5 h to 40 h, more preferably from 15 h to 25 h.

During the treatment according to (b), it is further preferred to suitably stir the aqueous solution. During (b), the stirring rate is kept essentially constant or changed, the treating with the liquid solvent system according to (b) thus being carried out at two or more different stirring rates.

After treating of the B-MWW with an aqueous solution according to (b), the thus obtained deborated zeolitic material is preferably suitably separated from the suspension. All methods of separating the deborated zeolitic material from the suspension are conceivable. These methods include, for example, filtration, ultrafiltration, diafiltration and centrifugation methods. A combination of two or more of these methods can be applied. According to a preferred embodiment of the present invention, the deboronated zeolitic material is preferably separated from the suspension by a filtration method.

After separating the deboronated zeolitic material, can be subjected to a washing step, wherein washing agents include, but are not limited to, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred. Water as sole washing agent is especially preferred.

After deboronation according to (b), at least a portion of Si comprised in the framework structure of the deboronated zeolitic material is isomorphously substituted by Zr.

As far as the compound in (c.1) is concerned, no specific restrictions exist. Preferably, the template compound is selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyl-trimethylammonium hydroxide, and a mixture of two or more thereof. More preferably, the template compound is piperidine.

As far as the Zr source used in (c.1) is concerned, no specific restrictions exist provided that Zr is introduced into the deboronated B-MWW. According to a preferred embodiment of the present invention, preferably, the Zr-source is selected from the group consisting of zirconium and zirconyl salts, more preferably from the group consisting of zirconium and zirconyl halides, zirconium hydroxide, zirconyl nitrate, zirconium alkoxides, and mixtures of two or more thereof, more preferably from the group consisting of zirconium and zirconyl bromide, chloride, fluoride, zirconyl nitrate, C1-C4 alkoxides of Zr, and mixtures of two or more thereof, more preferably from the group consisting of zirconium and zirconyl chloride, fluoride, zirconyl nitrate, C2-C3 alkoxides of Zr, and mixtures of two or more thereof, more preferably from the group consisting of zirconium and zirconyl chloride, zirconyl nitrate, C3 alkoxides of Zr, and mixtures of two or more thereof, more preferably from the group consisting of zirconyl chloride, zirconyl nitrate, Zn-n-propoxide, and mixtures of two or more thereof, wherein more preferably the Zr source is Zr-n-propoxide.

According to a particularly preferred embodiment of the present invention, the synthesis mixture according to (c.1) comprises the deboronated B-MWW obtained from (b), piperidine and Zr-n-propoxide.

During the treatment according to (c.1), it is further preferred to suitably stir the aqueous solution. During (c.1), the stirring rate is kept essentially constant or changed, the treating with the liquid solvent system according to (c.1) thus being carried out at two or more different stirring rates. For example, the stirring rate is in the range of from 50 to 300 r.p.m. (rounds per minute), such as from 100 to 250 r.p.m. or from 130 to 170 r.p.m.

According to a preferred embodiment of the present invention, the hydrothermal synthesis according to (c.2) is carried out at a temperature in the range of from 80 to 250° C., more preferably from 120 to 200° C., more preferably from 160 to 180° C. Further, the hydrothermal synthesizing according to (c.2) is preferably carried out for a period in the range of from 20 to 200 h, more preferably from 60 to 160 h, more preferably from 110 to 125 h.

After hydrothermal synthesis, the obtained Zr-containing zeolitic material is suitably separated from the mother liquor in step (c.3). All methods of separating the Zr-containing zeolitic material from its mother liquor are conceivable. These methods include, for example, filtration, ultrafiltration, diafiltration and centrifugation methods or, for instance, spray drying processes and spray granulation processes. A combination of two or more of these methods can be applied. According to the present invention, the Zr-containing zeolitic material is preferably separated from its mother liquor by filtration to obtain a filter cake which is preferably subjected to washing, preferably with water.

Preferably, stage (c.3) comprises drying the Zr-containing zeolitic material, wherein the drying is preferably carried out at a temperature in the range of from 100 to 180° C., more preferably from 110 to 140° C. Concerning the duration of drying the Zr-containing zeolitic material having an MWW-type framework structure, no specific restrictions exist. According to a preferred embodiment of the present invention, the drying is carried out for a period in the range of from 1 to 30 h, preferably from 6 to 24 h, more preferably from 14 to 18 h.

According to a preferred embodiment of the present invention, the separated and preferably dried Zr-containing zeolitic material obtained from (c) is subjected to stage (d) wherein the Zr-containing zeolitic material is treated with an aqueous solution having a pH of at most 5.

Preferably, in (d), the Zr-containing zeolitic material obtained from (c) is treated with an aqueous solution, which comprises an organic acid, preferably selected from the group consisting of oxalic acid, acetic acid, citric acid, methane sulfonic acid, and a mixture of two or more thereof, and/or an inorganic acid, preferably selected from the group consisting of phosphoric acid, sulphuric acid, hydrochloric acid, nitric acid, and a mixture of two or more thereof, the inorganic acid more preferably being nitric acid. Preferably, in (d), the aqueous solution has a pH in the range of from 0 to 5, preferably from 0 to 3, more preferably from 0 to 2. The pH values are to be understood as being determined with a pH sensitive glass electrode.

During the treatment according to (d), it is further preferred to suitably stir the aqueous solution. During (d), the stirring rate is kept essentially constant or changed, the treating with the liquid solvent system according to (d) thus being carried out at two or more different stirring rates. For example, the stirring rate is in the range of from 50 to 300 r.p.m. (rounds per minute), such as from 100 to 250 r.p.m. or from 150 to 190 r.p.m.

Concerning the temperature of the treating with the aqueous solution according to (d), no specific restrictions exist. Preferably, in (d), the Zr-containing zeolitic material is treated with the aqueous solution at a temperature in the range of from 50 to 175° C., preferably from 70 to 125° C., more preferably from 95 to 105° C. Preferably, in (d), the Zr-containing zeolitic material having an MWW-type framework structure is treated with the aqueous solution for a period in the range of from 1 to 40 h, more preferably from 12 to 24 h, more preferably from 18 to 22 h.

The treatment according to (d) preferably comprises suitably separating the Zr-containing zeolitic material from the aqueous solution. All methods of separating Zr-containing zeolitic material from the aqueous solution are conceivable. These methods include, for example, filtration, ultrafiltration, diafiltration and centrifugation methods or, for instance, spray drying processes and spray granulation processes. A combination of two or more of these methods can be applied. According to a preferred embodiment of the present invention, Zr-containing zeolitic material is preferably separated from the aqueous solution by filtration to obtain a filter cake which is preferably subjected to washing, preferably with water.

It was surprisingly found that the zeolitic materials obtained or obtainable according to the present invention wherein zeolitic material having a framework structure comprising $YO_2$, wherein at least a portion of Y comprised in the framework structure is isomorphously substituted by one or more elements X, can be used as such for any suitable purpose and in particular as a catalytically active material, such as a catalytically active material in a process for the preparation of butadiene according to the present invention.

Thus, the present invention also relates to the use of a zeolitic material having a framework structure comprising $YO_2$, Y standing for one or more tetravalent elements, wherein at least a portion of Y comprised in the framework structure is isomorphously substituted by one or more elements X, as a catalytically active material in a process for the preparation of butadiene, preferably from a gas stream comprising ethanol and optionally acetaldehyde.

According to a preferred embodiment of the present invention, the zeolitic material is used as a catalytically active material in a process for the preparation of butadiene, preferably from a gas stream comprising ethanol and optionally acetaldehyde. According to a particularly preferred embodiment of the present invention, the zeolitic material used as catalytically active material in a process for the preparation of butadiene preferably, preferably from a gas stream comprising ethanol and optionally acetaldehyde, is a zeolitic material having a framework structure comprising $YO_2$ as defined according to any of the particular and preferred embodiments of the present invention.

Quite unexpectedly it was found that the zeolitic materials obtained or obtainable according to the present invention can be used in a process for the preparation of butadiene according to the present invention, wherein the selectivity of the process relative to butadiene is at least 10%, preferably in the range of from 10 to 90%, more preferably from 20 to 80%, and more preferably from 30 to 70%.

Therefore, according to a particularly preferred embodiment of the present invention, the zeolitic materials according to the present invention are used in a process for the preparation of butadiene according to the present invention, wherein the selectivity of the process relative to butadiene is at least 10%, preferably in the range of from 10 to 90%, more preferably from 20 to 80%, more preferably from 30 to 70%. Within the meaning of the present invention, selectivity of the process relative to butadiene generally designates any suitable process for the preparation of butadiene, and accordingly the selectivity relative to butadiene obtained by such a process. It is, however, preferred according to the present invention, that the selectivity relative to butadiene designates a selectivity as obtained according to any of the particular and preferred embodiments of the process for the preparation of butadiene according to present invention as defined in the present application.

The present invention includes the following embodiments, wherein these include the specific combinations of embodiments as indicated by the respective interdependencies defined therein:

1. A gas-phase process for the preparation of butadiene comprising
    (i) providing a gas stream G-1 comprising ethanol;
    (ii) contacting the gas stream G-1 comprising ethanol with a catalyst, thereby obtaining a gas stream G-2 comprising butadiene,
    wherein the catalyst comprises a zeolitic material having a framework structure comprising $YO_2$, Y standing for one or more tetravalent elements, wherein at least a portion of Y comprised in the framework structure is isomorphously substituted by one or more elements X.

2. The process of embodiment 1, wherein the gas stream G-1 additionally comprises acetaldehyde.

3. The process of embodiment 2, wherein the molar ratio of ethanol to acetaldehyde in the gas stream G-1 is in the range of from 1:1 to 6:1, preferably from 2:1 to 3.5:1, more preferably from 2.5:1 to 2.9:1.

4. The process of embodiment 2 or 3, wherein 80 vol.-% or more of the gas stream G-1 comprises ethanol or of a mixture of ethanol and acetaldehyde, wherein preferably 90 vol.-% or more, more preferably 95 vol.-% or more of the gas stream G-1 comprises ethanol or of a mixture of ethanol and acetaldehyde.

5. The process of any of embodiments 1 to 4, wherein the molar ratio of Y:X in the framework structure ranges from 10:1 to 150:1, preferably from 20:1 to 80:1, more preferably from 30:1 to 50:1.

6. The process of any of embodiments 1 to 4, wherein the molar ratio of Y:X in the framework structure ranges from 50:1 to 700:1, preferably from 100:1 to 600:1, more preferably from 170:1 to 520:1.

7. The process of any of embodiments 1 to 6, wherein X stands for one or more trivalent, tetravalent, and/or pentavalent elements, wherein the one or more elements X are preferably selected from the group consisting of Zr, Ti, Sn, Ga, Nb, Ta, Sc, Ge, Al, B, Fe and combinations of two or more thereof, more preferably selected from the group consisting of Zr, Ti, Sn, Ga, Ge, Ta, and combinations of two or more thereof, more preferably selected from the croup consisting of Zr, Ti, Sn, Ta, and combinations of two or more thereof, even more preferably X stands for Zr and/or Ta.

8. The process of any of embodiments 1 to 7, wherein Y is selected from the group consisting of Si, Sn, Ti, Zr, Ge, and combinations of two or more thereof, preferably selected from the group consisting of Si, Ti, Ge, and combinations of two or more thereof, and more preferably Y stands for Si.

9. The process of any of embodiments 1 to 8, wherein the catalyst comprises a zeolitic material having a framework structure selected from the group consisting of BEA, MWW, MFI, MEL, MOR, RUT, DOH, MTN, FER, FAU, CDO, LEV, CHA, and combinations of two or more thereof, preferably selected from the group consisting of BEA, MWW, MFI, MEL and combinations of two or more thereof, more preferably selected from BEA and MWW.

10. The process of embodiment 9, wherein the catalyst comprises isomorphously substituted zeolite beta and/or Sn-MWW and/or Ta-MWW, preferably Zr-BEA and/or Ta-MWW.

11. The process of any of embodiments 1 to 9, wherein the zeolitic material comprised in the catalyst has an MWW framework structure, wherein Y is Si and X is Ti.

12. The process of embodiment 11, wherein the zeolitic material further comprises Zn as non-framework element, wherein Zn is preferably disposed on the catalyst by impregnation, more preferably by ion-exchange.

13. The process of any of embodiments 1 to 4, wherein the catalyst comprises the zeolitic material according to any of embodiments 33 to 37.

14. The process of any of embodiments 1 to 13, wherein contacting the gas stream G-1 with the catalyst is carried out at a temperature in the range of from 300 to 500° C., preferably from 325 to 425° C., more preferably from 350 to 400° C.

15. The process of any of embodiments 1 to 14, wherein contacting the gas stream G-1 with the catalyst is carried out at a pressure in the range of from 1 to 5 bar, preferably from 1 to 2 bar.
16. The process of any of embodiments 1 to 15, wherein contacting gas stream G-1 with the catalyst is carried out in continuous mode.
17. The process of any of embodiments 1 to 16, wherein contacting the gas stream G-1 with the catalyst is carried out in one ore more reactors, wherein the one ore more reactors contain the catalyst in the form of a fixed bed.
18. The process of any of embodiments 1 to 17, wherein prior to contacting the gas stream G-1 with the catalyst, the gas stream G-1 is heated, preferably to a temperature in the range of from 100 to 250° C., more preferably from 120 to 180° C.
19. The process of any of embodiments 1 to 18, wherein prior to contacting the gas stream G-1 with the catalyst, the catalyst is activated, preferably by heating.
20. The process of embodiment 19, wherein the catalyst is activated by heating to a temperature in the range of from 300 to 450° C., preferably from 325 to 425° C., more preferably from 350 to 400° C., preferably for a period in the range of from 5 to 120 min, more preferably from 10 to 60 min, more preferably from 20 to 40 min.
21. The process of embodiment 19 or 20, wherein the catalyst is heated with a temperature ramp in the range of from 0.5 to 10 K/min, preferably 1 to 5 K/min, preferably from 1 to 3 K/min.
22. The process of any of embodiments 19 to 21, wherein the catalyst is activated in the one or more reactors.
23. The process of any of embodiments 19 to 22, wherein during heating the catalyst is flushed with an inert gas, preferably with an inert gas selected from the group consisting of helium, nitrogen, argon, and mixtures of two or more thereof, wherein the inert gas is more preferably nitrogen.
24. The process of any of embodiments 1 to 23, wherein the gas stream G-2 contains butadiene in an amount of from 10 to 90 vol-%, preferably from 20 to 80 vol-%, more preferably from 30 to 70 vol-%, based on the total volume of the gas stream G-2.
25. The process of any of embodiments 1 to 24, further comprising
   (iii) separating butadiene from the gas stream G-2, thereby obtaining a purified gas stream G-3 comprising butadiene, wherein the separation is preferably achieved by thermal separation, more preferably by distillation.
26. The process of any of embodiments 1 to 25, wherein the gas stream G-2 further comprises diethyl ether, and wherein the diethyl ether is separated from the gas stream G-2, preferably by thermal separation, more preferably by distillation, and recycling the separated diethyl ether to the gas-phase process for the preparation of butadiene, preferably as component of the gas stream G-1.
27. The process of embodiment 26, wherein the gas stream G-2 contains the diethyl ether in an amount of from 1 to 65 vol-%, preferably from 1 to 35 vol-%, more preferably from 2-20 vol-%, based on the total volume of the gas stream G-2.
28. The process of embodiment 26 or 27, further comprising hydrolyzing at least a portion of the separated diethyl ether to ethanol prior to its recycling to the gas-phase process for the preparation of butadiene, preferably as component of the gas stream G-1.
29. The process of embodiment 28, wherein the separated diethyl ether is hydrolyzed under acidic conditions, more preferably in the presence of a solid catalyst.
30. The process of any of embodiments 1 to 29, wherein the gas stream G-2 further comprises crotonaldehyde.
31. The process of embodiment 30, wherein the gas stream G-2 contains the crotonaldehyde in an amount of from 0.1 to 15 vol-%, preferably from 0.5 to 10 vol-%, more preferably from 1 to 5 vol-%, based on the total volume of the gas stream G-2.
32. The process of any of embodiments 1 to 31, further comprising regenerating the catalyst, preferably by thermal treatment in the presence of oxygen, wherein the thermal treatment is preferably performed at a temperature in the range of from 100 to 700° C., preferably from 350 to 600° C., more preferably from 450 to 570° C.
33. A zeolitic material having a framework structure comprising $YO_2$, Y standing for one or more tetravalent elements, wherein at least a portion of Y comprised in the framework structure is isomorphously substituted by one or more elements X, and wherein the zeolitic material has an X-ray powder diffraction pattern comprising at least the following reflections:

| Intensity (%) | Diffraction angle 2 theta/° [Cu K(alpha 1)] |
|---|---|
| 67.0-87.0 | 15.16 ± 0.3 |
| 79.8-99.8 | 15.82 ± 0.3 |
| 45.3-65.3 | 22.47 ± 0.3 |
| 100 | 23.88 ± 0.3 |
| 52.3-72.3 | 27.06 ± 0.3 |
| 75.0-95.0 | 27.21 ± 0.3 | wherein 100% relates to the intensity of the maximum peak in the X-ray powder diffraction pattern.
34. The zeolitic material of embodiment 33, wherein the molar ratio of Y:X in the framework structure ranges from 100:1 to 700:1, preferably from 300:1 to 600:1, more preferably from 450:1 to 550:1.
35. The zeolitic material of embodiment 33 or 34, wherein X stands for one or more trivalent, tetravalent, and/or pentavalent elements, preferably selected from the group consisting of Zr, Ti, Sn, Ga, Nb, Ta, Sc, Ge, Al, B, Fe and combinations of two or more thereof, more preferably selected from the group consisting of Zr, Ti, Sn, Ga, Ge, Ta, and combinations of two or more thereof, more preferably selected from the croup consisting of Zr, Ti, Sn, Ta, and combinations of two or more thereof, even more preferably X stands for Zr.
36. The zeolitic material of any of embodiments 33 to 35, wherein Y is selected from the group consisting of Si, Sn, Ti, Zr, Ge and combinations of two or more thereof, preferably selected from the group consisting of Si, Ti, Ge, and combinations of two or more thereof, more preferably Y stands for Si.
37. The zeolitic material of any of embodiments 33 to 36, wherein the zeolitic material has a BET specific surface area of at least 20 $m^2/g$, and preferably a BET specific surface area in the range of from 20 to 600 $m^2/g$, more preferably in the range of from 30 to 500 $m^2/g$, wherein the specific surface area is determined according to DIN 66131.
38. Use of a zeolitic material having a framework structure comprising $YO_2$, Y standing for one or more tetravalent elements, wherein at least a portion of Y comprised in the framework structure is isomorphously substituted by one or more elements X, as a catalytically active material in a process for the preparation of butadiene, preferably from a gas stream comprising ethanol and optionally acetaldehyde.

39. The use of embodiment 38, wherein the zeolitic material is a zeolitic material having a framework structure comprising $YO_2$ as defined in any of embodiments 5 to 12 or in any of embodiments 33 to 37.

40. The use of embodiment 38 or 39, wherein the selectivity of the process relative to butadiene is at least 10%, preferably in the range of from 10 to 90%, more preferably from 20 to 80%, more preferably from 30 to 70%.

EXAMPLES

Figure 1:
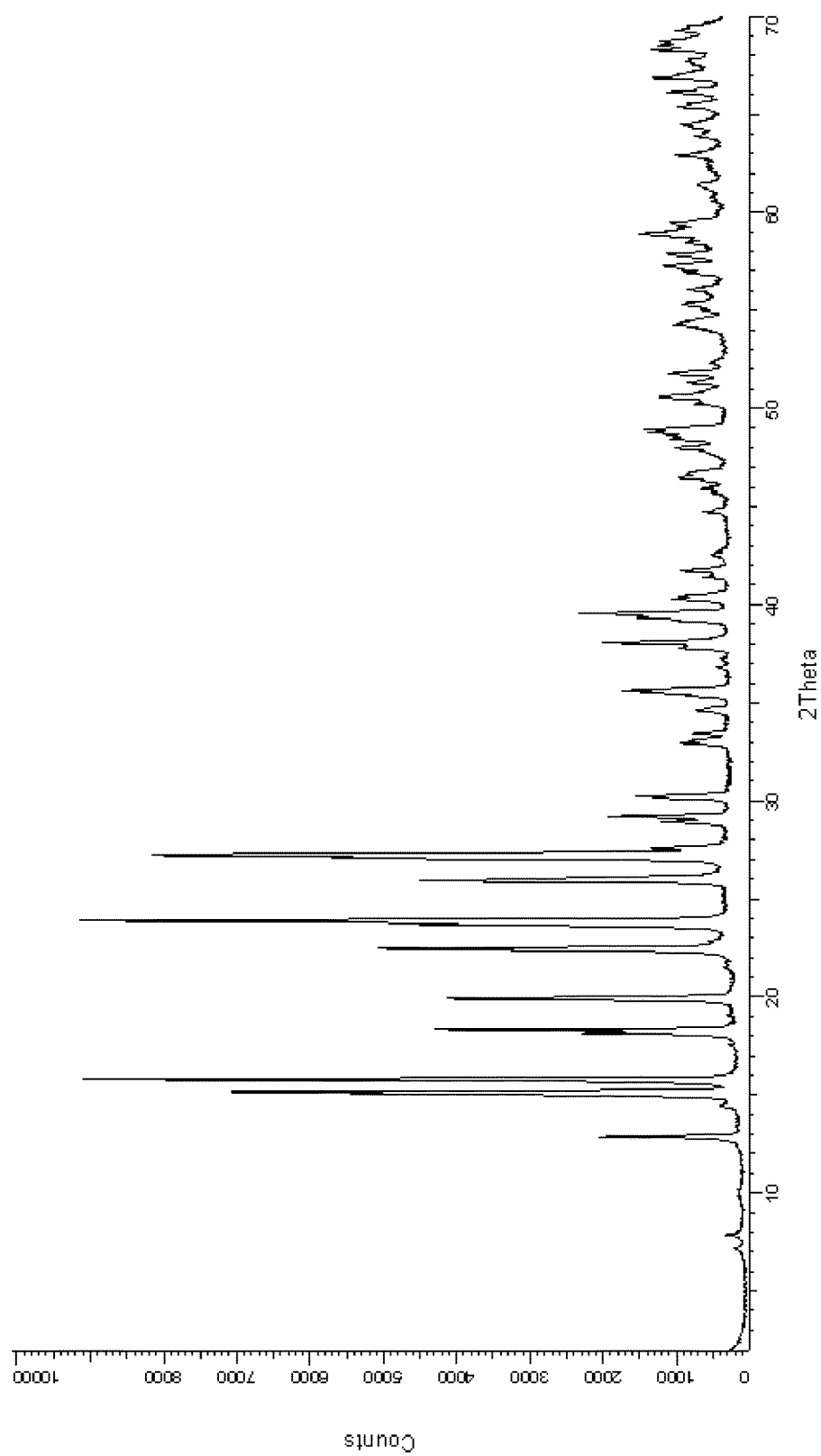
FIG. 1: shows the X-ray diffraction (XRD) pattern (measured using Cu K alpha-1 radiation) of the crystalline zirconium-containing silicate (Zr-silicate) obtained from Example 3. In the figure, the diffraction angle 2 theta in ° is shown along the abscissa and the intensities are plotted along the ordinate.

Reference Example 1: Determination of the Crystallinity and of the Lattice Parameter c of Zeolitic Materials Having an MWW-Framework Structure The crystallinity and the lattice parameter c of the zeolitic materials according to the present invention were determined by XRD analysis. The data are collected using a standard Bragg-Brentano diffractometer with a Cu-X-ray source and an energy dispersive point detector. The angular range of 2° to 70° (2 theta) is scanned with a step size of 0.02°, while the variable divergence slit is set to a constant illuminated sample length of 20 mm. The data are then analyzed using TOPAS V4 software, wherein the sharp diffraction peaks are modelled using a Pawley fit containing a unit cell with the following starting parameters: a=14.4 Angstrom and c=25.2 Angstrom in the space group P6/mmm. These are refined to fit the data. Independent peaks are inserted at the following positions. 8.4°, 22.4°, 28.2° and 43°. These are used to describe the amorphous content. The crystalline content describes the intensity of the crystalline signal to the total scattered intensity. Included in the model are a linear background, Lorentz and polarization corrections, lattice parameters, space group and crystallite size.

Reference Example 2: Determination of the Crystallinity of Zeolitic Materials Having a BEA-Framework Structure The crystallinity of the zeolitic materials according to the present invention was determined by XRD analysis, wherein the crystallinity of a given material is expressed relative to a reference zeolitic material wherein a single reflection of the two zeolitic materials are compared. The reference zeolitic material was zeolite ammonium beta powder commercially available under the CAS registry number 1318-02-1. The determination of the crystallinities was performed on a D8 Advance series 2 diffractometer from Bruker AXS. The diffractometer was configured with an opening of the divergence aperture of 0.1° and a Lynxeye detector. The samples as well as the reference zeolitic material were measured in the range from 19° to 25° (2 Theta). After baseline correction, the areas of the reflections were determined by making use of the evaluation software EVA (from Bruker AXS). The ratios of the areas are given as percentage values.

Reference Example 3: Determination of Dv50

1. Sample Preparation
    1.0 g of the micropowder is suspended in 100 g deionized water and stirred for 1 min.
2. Apparatus and Respective Parameters Used
    Mastersizer S long bed version 2.15, ser. No. 33544-325; supplier: Malvern Instruments GmbH, Herrenberg, Germany
    focal width: 300 RF mm
    beam length: 10.00 mm
    module: MS17
    shadowing: 16.9
    dispersion model: 3$$D
    analysis model: polydisperse
    correction: none Reference Example 4: Conversion of a Mixture of Ethanol and Acetaldehyde to Butadiene Preparation of the Catalyst Samples:
Before testing catalyst samples were compacted using pressure of 25 kN and sieved to particle size in the range of from 315 to 500 μm.
Set-Up:
Experiments were conducted in a 16-fold Test-unit. For feed-dosage a mixture of acetaldehyde and ethanol was pumped to an evaporator in which it is heated to 125° C. within a gas stream of nitrogen. The trace-heated (170° C.) feed stream is then distributed to all 16 reactor tubes. Within each reactor tube (stainless steel; 400 mm long and 4 mm ID) the catalyst sieve fraction (1 cc) is guarded by an upper and a lower inert layer consisting of quartz (315-500 μm, 2 cc). By means of a multiport-selection valve the trace-heated (200° C.) effluent of each reactor is led to the GC/MS for product analysis.

Activation of the Catalyst

For activation, samples are heated at 375° C. for 30 min under nitrogen.

Performance

A mixture of ethanol and acetaldehyde (molar ratio 2.75:1) was evaporated and mixed with nitrogen to obtain a feed composition of 90 vol.-% ethanol/acetaldehyde and 10 vol.-% nitrogen. The thus obtained feed stream was converted over the catalyst to butadiene at a temperature of 375° C. and under a pressure in the range of from 1 to 2 bar and with LHSV (liquid hourly space velocity) of 0.6 h$^{-1}$. The gaseous product mixture was analyzed by online gas chromatography.

LHSV (liquid hourly space velocity): 0.6 h$^{-1}$

Average conversions and selectivities over an operation time of 110 h were determined, wherein the conversions and selectivities were determined in 8 h interval.

Reference Example 5: Measurement of the UV-VIS Spectra

The measurement of the UV-VIS spectra were performed using a Lambda 950 spectrophotomerter from PerkinElmer with 150 mm integrating spheres, wherein a spectralon white standard from the firm Labsphere was used as reference.

Example 1: Synthesis of Zirconium-Containing Zeolitic Material Having a BEA Frame Work Structure (Zr-BEA)

In a round bottom flask 86.30 g of tetraethylorthosilicate (TEOS) was added together with 97.48 g of tetraethylammonium hydroxide (TEAOH). 1.33 g of ZrOCl$_2$ and 3.31 g distilled water were added to the suspension. The alcohol was distilled under stirring at 95° C. After distillation the mixture was cooled to room temperature and transferred to a Teflon liner of a Berghof autoclave (250 mL). To the mixture 11.59 g of an aqueous hydrogen fluoride solution (40 weight-% in water) and 3.02 g of seeds of a dealuminated zeolitic material having a BEA framework structure were added. The autoclave was closed and the zeolite was hydrothermally synthesized in a static oven for 20 days at 140° C. After this period, the autoclave was cooled the room temperature and the solid was separated by filtration and washed with distilled water until the washing water had a pH of 7. The solid was dried in a static oven at 100° C. for 16 h, and calcined at 580° C. for 4 h.

Characterization

The obtained zeolitic material had a zirconium content of 0.75 weight-%, a silicon content of 45.0 weight-% and a crystallinity of 124%, determined by XRD. The BET specific surface area determined via nitrogen adsorption at 77 K according to DIN 66131 was 456 m$^2$/g.

Example 2: Synthesis of Zirconium-Containing Zeolitic Material Having a BEA Frame Work Structure (Zr-BEA)

In a round bottom flask 129.60 g of tetraethylorthosilicate (TEOS) was added together with 146.39 g or tetraethylammonium hydroxide (TEAOH). 1.00 g of ZrOCl$_2$ and 5.59 g distilled water were added to the suspension. The alcohol was distilled under stirring at 95° C. After distillation the mixture was cooled to room temperature and transferred to a Teflon liner of a Berghof autoclave (250 mL). To the mixture 17.40 g of an aqueous hydrogen fluoride solution (40 wt.-% in water) and 4.54 g of seeds of dealuminated-Beta zeolite were added. The autoclave was closed and the zeolite was hydrothermally synthesized in a static oven for 20 days a 140° C. After this period, the autoclave was cooled the room temperature and the solid was separated by filtration and washed with distilled water until the washing water had a pH of 7. The solid was dried in a static oven at 100° C. for 16 h, and calcined at 580° C. for 4 h.

Characterization

The obtained zirconium-containing zeolitic material having a BEA framework structure had a zirconium content of 0.48 weight-%, a silicon content of 46.0 weight-% and a crystallinity of 124%, determined by XRD. The BET specific surface area determined via nitrogen adsorption at 77 K according to DIN 66131 was 472 m$^2$/g.

Example 3: Synthesis of a Crystalline Zirconium-Containing Silicate (Zr-Silicate)

Example 3.1: Synthesis of a Boron-Containing Zeolitic Material Having an MWW Framework Structure (B-MWW)

15.75 kg de-ionized water and 6.08 kg piperidin were introduced in a stirring pressure vessel. Under stirring 3.63 kg boric acid were added and the suspension was stirred for additional 30 min. To the resulting solution, 3.5 kg Aerosil 200 were added in portions and the suspension was further stirred for 2 h. Finally, the crystallization vessel was heated to 170° C. within 2 h under autogenous pressure and stirred at 150 rpm. The temperature of 170° C. was kept essentially constant for 120 h. During these 120 h, the mixture was stirred at 150 rpm. Subsequently, the mixture was cooled to a temperature in the range of from 50 to 60° C. The aqueous suspension containing the boron-containing zeolitic material having an MWW framework structure (B-MWW) had a pH of 11.3 as determined via measurement with a pH electrode. From said suspension, the B-MWW was separated by filtration. The filter cake was washed with de-ionized water until the washing water had a conductivity of less than 700 microSiemens/cm. The filtercake was dried in a static oven at 100° C. for 16 h and the dried powder was calcined at 600° C. for 16 h.

Characterization

The obtained B-MWW had a boron content of 1.4 weight-%, a silicon content of 42 weight-% and a total organic carbon (TOC) content of 0.01 weight-%.

Example 3.2: Deboronation

The B-MWW obtained according to Example 3.2 was deboronated following the below procedure:

122.5 kg of an aqueous HNO$_3$ solution (30 weight-% in water) were introduced together with 4.08 kg of the B-MWW in a vessel equipped with a reflux condenser. The suspension was stirred and heated to 100° C. and kept for 20 h under reflux conditions. Afterwards the mixture was cooled down and the solid was recovered by filtration and washed with distilled water until the washing water had a pH of 7. The filtercake was afterwards dried in a static oven at 120° C. for 16 h.

Characterization

The obtained deboronated zeolitic material had a boron content of 0.07 weight-% and a silicon content of 41.0 weight-%

Example 3.3: Incorporation of Zirconium 540 g of water and 260.64 g of piperidine were introduced in a glass flask. The mixture was stirred at 200 rpm and 24.56 g of Zirconium-n-propoxide were added. The obtained mixture was further stirred for 20 min before drop-wise addition of 180 g of the deboronated zeolitic material having an MWW framework structure obtained according to Example 3.2. The suspension was further stirred for 2 h at 200 rpm until a gel was obtained. The formed gel was transferred to an autoclave. The autoclave was heated to 170° C. and kept at this temperature for 120 h under stirring at 150 rpm. Subsequently, the autoclave was cooled down and the solid was separated by filtration and washed until the washing water had a pH of 7. The filtercake was dried in a static oven at 120° C. for 16 h.

Characterization

The obtained zirconium-containing zeolitic material had a zirconium content of 3.2 weight-% and a silicon content of 38.5 weight-%.

Example 3.4: Acid Treatment of the Zirconium Containing Zeolitic Material 4200 g of an aqueous $HNO_3$ solution (30 weight-% in water) was provided in a 10 L flask. To this solution the zirconium-containing silicate obtained according to Example 3.3 was added and the mixture was heated to 100° C. for 20 h under stirring with 170 rpm. Afterwards the suspension was filtered and washed until the washing water had a pH of 7. The filtercake was dried in a static oven for 16 h at 120° C. and calcined at 550° C. for 10 h.

Characterization

The obtained zeolitic material had a zirconium content of 0.27 weight-% and a silicon content of 43 weight-%. The BET specific surface area determined via nitrogen adsorption at 77 K according to DIN 66131 was 38 m²/g. The XRD of the obtained zeolitic material is shown in FIG. 1. The obtained zeolitic material has an XRD pattern having the following reflections:

| Diffraction angle 2 theta/° [Cu K(alpha 1)] | Intensity [%] |
| --- | --- |
| 7.2 ± 0.1 | 2.3 ± 0.1 |
| 7.9 ± 0.1 | 3.6 ± 0.1 |
| 12.9 ± 0.1 | 22.6 ± 0.1 |
| 14.5 ± 0.1 | 4.3 ± 0.1 |
| 15.2 ± 0.1 | 77.0 ± 0.1 |
| 15.9 ± 0.1 | 98.6 ± 0.1 |
| 18.1 ± 0.1 | 25.0 ± 0.1 |
| 18.3 ± 0.1 | 47.0 ± 0.1 |
| 19.9 ± 0.1 | 44.4 ± 0.1 |
| 22.4 ± 0.1 | 35.7 ± 0.1 |
| 22.5 ± 0.1 | 55.3 ± 0.1 |
| 23.7 ± 0.1 | 49. ± 0.12 |
| 23.9 ± 0.1 | 100 |
| 25.9 ± 0.1 | 49.1 ± 0.1 |
| 27.1 ± 0.1 | 62.3 ± 0.1 |
| 27.2 ± 0.1 | 89.0 ± 0.1 |
| 27.6 ± 0.1 | 14. ± 0.16 |
| 28.9 ± 0.1 | 13.0 ± 0.1 |
| 29.2 ± 0.1 | 21.6 ± 0.1 |
| 30.2 ± 0.1 | 16.6 ± 0.1 |
| 32.9 ± 0.1 | 9.9 ± 0.1 |
| 33.1 ± 0.1 | 9.0 ± 0.1 |
| 33.4 ± 0.1 | 8.4 ± 0.1 |
| 34.6 ± 0.1 | 7.6 ± 0.1 |
| 35.5 ± 0.1 | 16.0 ± 0.1 |
| 35.6 ± 0.1 | 19.1 ± 0.1 |
| 36.7 ± 0.1 | 5.0 ± 0.1 |
| 37.8 ± 0.1 | 10. ± 0.16 |
| 38.0 ± 0.1 | 21. ± 0.13 |
| 39.1 ± 0.1 | 10. ± 0.15 |
| 39.3 ± 0.1 | 17.0 ± 0.1 |
| 39.5 ± 0.1 | 25.0 ± 0.1 |
| 40.2 ± 0.1 | 11.2 ± 0.1 |
| 40.4 ± 0.1 | 10.2 ± 0.1 |
| 41.4 ± 0.1 | 6.5 ± 0.1 |
| 41,.7 ± 0.1 | 9.2 ± 0.1 |
| 42.5 ± 0.1 | 5.6 ± 0.1 |
| 42.8 ± 0.1 | 4.4 ± 0.1 |
| 44.7 ± 0.1 | 6.7 ± 0.1 |
| 45.6 ± 0.1 | 5.6 ± 0.1 |
| 45.9 ± 0.1 | 7.1 ± 0.1 |
| 46.5 ± 0.1 | 10.5 ± 0.1 |
| 46.7 ± 0.1 | 9.5 ± 0.1 |
| 47.9 ± 0.1 | 11.0 ± 0.1 |
| 48.4 ± 0.1 | 12.0 ± 0.1 |
| 48.6 ± 0.1 | 12.4 ± 0.1 |
| 48.8 ± 0.1 | 15.3 ± 0.1 |
| 48.9 ± 0.1 | 15.8 ± 0.1 |
| 50.2 ± 0.1 | 8.2 ± 0.1 |
| 50.5 ± 0.1 | 13.5 ± 0.1 |
| 51.3 ± 0.1 | 9.1 ± 0.1 |
| 51.8 ± 0.1 | 11.9 ± 0.1 |
| 52.3 ± 0.1 | 6.1 ± 0.1 |
| 54.2 ± 0.1 | 10.9 ± 0.1 |
| 55.2 ± 0.1 | 10.1 ± 0.1 |
| 55.4 ± 0.1 | 9.1 ± 0.1 |
| 56.0 ± 0.1 | 8.7 ± 0.1 |
| 56.9 ± 0.1 | 9.7 ± 0.1 |
| 57.2 ± 0.1 | 12.9 ± 0.1 |
| 57.8 ± 0.1 | 11.9 ± 0.1 |
| 58.4 ± 0.1 | 9.2 ± 0.1 |
| 58.9 ± 0.1 | 16.3 ± 0.1 |
| 59.4 ± 0.1 | 11.9 ± 0.1 |
| 61.4 ± 0.1 | 7.7 ± 0.1 |
| 62.9 ± 0.1 | 10.6 ± 0.1 |
| 63.8 ± 0.1 | 7.7 ± 0.1 |
| 64.3 ± 0.1 | 9.1 ± 0.1 |
| 64.4 ± 0.1 | 10.6 ± 0.1 |
| 65.3 ± 0.1 | 10.1 ± 0.1 |
| 65.5 ± 0.1 | 9.1 ± 0.1 |
| 66.1 ± 0.1 | 12.7 ± 0.1 |
| 66.3 ± 0.1 | 8.1 ± 0.1 |
| 66.8 ± 0.1 | 14.7 ± 0.1 |
| 67.0 ± 0.1 | 10.9 ± 0.1 |
| 67.6 ± 0.1 | 8.9 ± 0.1 |
| 68.2 ± 0.1 | 14.8 ± 0.1 |
| 68.5 ± 0.1 | 13.2 ± 0.1 |
| 68.7 ± 0.1 | 13.0 ± 0.1 |
| 69.2 ± 0.1 | 10.7 ± 0.1 |
| 69.4 ± 0.1 | 9.1 ± 0.1 |

Example 4: Synthesis of ZnTi-MWW

Example 4: 1 Preparation of Boron-Containing MWW 470.4 kg de-ionized water were provided in a vessel. Under stirring at 70, 162.5 kg boric acid were suspended in the water. The suspension was stirred for another 3 h. Subsequently, 272.5 kg piperidine were added, and the mixture was stirred for another hour. To the resulting solution, 392.0 kg Ludox® AS-40 were added, and the resulting mixture was stirred at 70 rpm for another hour.

The finally obtained mixture was transferred to a crystallization vessel and heated to 170° C. within 5 h under autogenous pressure and under stirring (50 rpm). The temperature of 170° C. was kept essentially constant for 120 h; during these 120 h, the mixture was stirred at 50 rpm. Subsequently, the mixture was cooled to a temperature of from 50-60° C. within 5 h. The aqueous suspension containing B-MWW had a pH of 11.3 as determined via measurement with a pH electrode.

From said suspension, the B-MWW was separated by filtration. The filter cake was then washed with de-ionized water until the washing water had a conductivity of less than 700 microSiemens/cm The thus obtained filter cake was subjected to spray-drying in a spray-tower with the following spray-drying conditions:
drying gas, nozzle gas: technical nitrogen
temperature drying gas:
    temperature spray tower (in): 288-291° C.
    temperature spray tower (out): 157-167° C.
    temperature filter (in): 150-160° C.
    temperature scrubber (in): 40-48° C.
    temperature scrubber (out): 34-36° C.
pressure difference filter: 8.3-10.3 mbar
nozzle:
    two-component nozzle supplier Gerig; size 0
    nozzle gas temperature: room temperature
    nozzle gas pressure: 2.5 bar
operation mode: nitrogen straight
apparatus used: spray tower with one nozzle
configuration: spray tower-filter-scrubber
gas flow: 1,900 kg/h
filter material: Nomex® needle-felt 20 m$^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 650° C. for 2 h.

Characterization

The calcined material had a boron content of 1.9 weight-%, a silicon content of 41 weight-%, and a total organic carbon content of 0.18 weight-%. The crystallinity determined by XRD was 74%, BET specific surface area determined via nitrogen adsorption at 77 K according to DIN 66131 was 448 m$^2$/g, pore volume determined by HG porosimetry according to DIN 66133 was 5.9 mL/g, particle size distribution of the sprayed-dried particle determined by Malvern Dv50 was 26.9 μm.

4.2 Preparation of Deborated MWW a) Deboration

Based on the spray-dried material obtained according to section 4.1 above, 4 batches of deborated zeolite MWW were prepared. In each of the first 3 batches, 35 kg of the spray-dried material obtained according to section 4.1 and 525 kg water were employed. In the fourth batch, 32 kg of the spray-dried material obtained according to section 4.1 and 480 kg water were employed. In total, 137 kg of the spray-dried material obtained according to section 4.1 and 2025 kg water were employed.

For each batch, the respective amount of water was passed into a vessel equipped with a reflux condenser. Under stirring at 40 r.p.m., the given amount of the spray-dried material was suspended into the water. Subsequently, the vessel was closed and the reflux condenser put into operation. The stirring rate was increased to 70 r.p.m. Under stirring at 70 r.p.m., the content of the vessel was heated to 100° C. within 10 h and kept at this temperature for 10 h. Then, the content of the vessel was cooled to a temperature of less than 50° C. The resulting deborated zeolitic material of structure type MWW was separated from the suspension by filtration under a nitrogen pressure of 2.5 bar and washed four times with deionized water. After the filtration, the filter cake was dried in a nitrogen stream for 6 h.

The deborated zeolitic material obtained in 4 batches (625.1 kg nitrogen-dried filter cake in total) had a residual moisture content of 79%, as determined using an IR (infrared) scale at 160° C.

b) Spray-Drying of the Nitrogen-Dried Filter Cake

From the nitrogen-dried filter cake having a residual moisture content of 79% obtained according to section a) above, an aqueous suspension was prepared with de-ionized water, the suspension having a solid content of 15 wt.-%. This suspension was subjected to spray-drying in a spray-tower with the following spray-drying conditions:

drying gas, nozzle gas: technical nitrogen
temperature drying gas:
    temperature spray tower (in): 304° C.
    temperature spray tower (out): 147-150° C.
    temperature filter (in): 133-141° C.
    temperature scrubber (in): 106-114° C.
    temperature scrubber (out): 13-20° C.
pressure difference filter: 1.3-2.3 mbar
nozzle:
    two-component nozzle: supplier Niro, diameter 4 mm
    nozzle gas throughput: 23 kg/h
    nozzle gas pressure: 2.5 bar
operation mode: nitrogen straight
apparatus used: spray tower with one nozzle
configuration: spray tower-filter-scrubber
gas flow: 550 kg/h
filter material: Nomex® needle-felt 10 m$^2$
dosage via flexible tube pump: VF 10 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

Characterization

The spray-dried boron-containing zeolitic material had a boron content of 0.08 weight-%, a silicon content of 42 weight-%, and a total organic carbon content of 0.23 weight-%. The BET specific surface area determined via nitrogen adsorption at 77 K according to DIN 66131 was 476 m$^2$/g and the crystallinity, determined by XRD was 81%.

Example 4.3: Preparation of TiMWW

Based on the deborated MWW material as obtained according to section 4.2, a zeolitic material of structure type MWW containing titanium was prepared, referred to in the following as TiMWW. The synthesis was performed in two experiments, described in the following as a) and b):

a) First Experiment
Starting materials: deionized water: 244.00 kg
  piperidine: 118.00 kg
  tetrabutylorthotitanate: 10.90 kg
  deborated zeolitic material: 54.16 kg
54.16 kg of the deborated zeolitic material of structure type MWW were transferred in to a first vessel A.
In a second vessel B, 200.00 kg deionized water were transferred and stirred at 80 r.p.m. 118.00 kg piperidine were added under stirring, and during addition, the temperature of the mixture increased for about 15° C. Subsequently, 10.90 kg tetrabutylorthotitanate and 20.00 kg deionized water were added. Stirring was then continued for 60 min.
The mixture of vessel B was then transferred into vessel A, and stirring in vessel A was started (70 r.p.m.). 24.00 kg deionized water were filled into vessel A and transferred to vessel B.
The mixture in vessel B was then stirred for 60 min. at 70 r.p.m. At the beginning of the stirring, the pH of the mixture in vessel B was 12.6, as determined with a pH electrode.
After said stirring at 70 r.p.m., the frequency was decreased to 50 r.p.m., and the mixture in vessel B was heated to a temperature of 170° C. within 5 h. At a constant stirring rate of 50 r.p.m., the temperature of the mixture in vessel B was kept at an essentially constant temperature of 170° C. for 120 h under autogenous pressure. During this crystallization of TiMWW, a pressure increase of up to 10.6 bar was observed. Subsequently, the obtained suspension containing TiMWW having a pH of 12.6 was cooled within 5 h.
The cooled suspension was subjected to filtration, and the separated mother liquor was transferred to waste water discharge. The filter cake was washed four times with deionized water under a nitrogen pressure of 2.5 bar. After the last washing step, the filter cake was dried in a nitrogen stream for 6 h.
From 246 kg of said filter cake, an aqueous suspension was prepared with deionized water, the suspension having a solid content of 15 weight-%. This suspension was subjected to spray-drying in a spray-tower with the following spray-drying conditions:
drying gas, nozzle gas: technical nitrogen
temperature drying gas:
  temperature spray tower (in): 304° C.
  temperature spray tower (out): 147-152° C.
  temperature filter (in): 133-144° C.
  temperature scrubber (in): 111-123° C.
  temperature scrubber (out): 12-18° C.
pressure difference filter: 1.8-2.8 mbar
nozzle:
  top-component nozzle: supplier Niro, diameter 4 mm
  nozzle gas throughput: 23 kg/h
  nozzle gas pressure: 2.5 bar
operation mode: nitrogen straight
apparatus used: spray tower with one nozzle
configuration: spray tower-filter-scrubber
gas flow: 550 kg/h
filter material: Nomex® needle-felt 10 m²
dosage via flexible tube pump: VF 10 (supplier: Verder)
The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.
Characterization
The spray-dried TiMWW material obtained from the first experiment had a silicon content of 37 weight-%, a titanium content of 2.4 weight-%, and a total organic carbon content of 7.5 weight-%.

b) Second Experiment
The second experiment was carried out in the same way as the first experiment described in section a) above. The spray-dried TiMWW material obtained from the second experiment had a silicon content of 36 weight-%, a titanium content of 2.4 weight-%, a total organic carbon content of 8.0 weight-%

Example 4.4: Add Treatment of TiMWW

Each of the two spray-dried TiMWW materials as obtained in the first and the second experiment described in sections 4.3 a) and 4.3 b) above was subjected to acid treatment as described in the following in sections a) and b). In section c) hereinunder, it is described how a mixture of the materials obtained from a) and b) are spray-dried. In section d) hereinunder, it is described how the spray-dried material is calcined.

a) Acid Treatment of the Spray-Dried Material Obtained According to Section 4.3.a)
Starting materials: deionized water: 690.0 kg
  nitric acid: (53%): 900.0 kg
  spray-dried Ti-MWW 4.3. a): 53.0 kg
670.0 kg deionized water were filled in a vessel. 900 kg nitric acid were added, and 53.0 kg of the spray-dried TiMWW were added under stirring at 50 r.p.m. The resulting mixture was stirred for another 15 min. Subsequently, the stirring rate was increased to 70 r.p.m. Within 1 h, the mixture in the vessel was heated to 100° C. and kept at this temperature and under autogenous pressure for 20 h under stirring. The thus obtained mixture was then cooled within 2 h to a temperature of less than 50° C. The cooled mixture was subjected to filtration, and the filter cake was washed six times with deionized water under a nitrogen pressure of 2.5 bar. After the last washing step, the filter cake was dried in a nitrogen stream for 10 h. The washing water after the sixth washing step had a pH of about 2.7. 225.8 kg dried filter cake were obtained.

b) Acid Treatment of the Spray-Dried Material Obtained According to Section 4.3.b)
Starting materials: deionized water: 690.0 kg
  nitric acid: (53%): 900.0 kg
  spray-dried Ti-MWW 4.3. b): 55.0 kg
The acid treatment of the spray-dried material obtained according to section 4.3.b) was carried in the same way as the acid treatment of the spray-dried material obtained according to section 4.3.a) as described in section 4.4 a). The washing water after the sixth washing step had a pH of about 2.7. 206.3 kg dried filter cake were obtained.

c) Spray-Drying of the Mixture of the Materials Obtained from 4.4.a) and 4.4 b)

From 462.1 kg of the mixture of the filter cakes obtained from 4.4.a) and 4.4 b), an aqueous suspension was prepared with deionized water, the suspension having a solid content of 15 weight-%. This suspension was subjected to spray-drying in a spray-tower with the following spray-drying conditions:

drying gas, nozzle gas: technical nitrogen
temperature drying gas:
    temperature spray tower (in): 304-305° C.
    temperature spray tower (out): 151° C.
    temperature filter (in): 141-143° C.
    temperature scrubber (in): 109-118° C.
    temperature scrubber (out): 14-15° C.
pressure difference filter: 1.7-3.8 mbar
nozzle:
    two-component nozzle: supplier Niro, diameter 4 mm
    nozzle gas throughput: 23 kg/h
    nozzle gas pressure: 2.5 bar
operation mode: nitrogen straight
apparatus used: spray tower with one nozzle
configuration: spray tower-filter-scrubber
gas flow: 550 kg/h
filter material: Nomex® needle-felt 10 m$^2$
dosage via flexible tube pump: VF 10 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

Characterization

The spray-dried acid-treated TiMWW material had a silicon content of 42 weight-%, a titanium content of 1.6 weight-%, and a total organic carbon content of 1.7 weight-%. The BET specific surface area determined via nitrogen adsorption at 77 K according to DIN 66131 was 435 m$^2$/g and the crystallinity, determined by XRD was 80%.

d) Calcination of the Spray-Dried Material Obtained According to 4.4. c)

The spray-dried material was then subjected to calcination at 650° C. in a rotary furnace for 2 h.

Characterization

The calcined material had a silicon content of 42.5 weight-%, a titanium content of 1.6 weight-% and a total organic carbon content of 0.15 weight-%. The Langmuir surface are determined via nitrogen adsorption at 77 K according to DIN 66134 was 612 m$^2$/g, the BET specific surface area determined via nitrogen adsorption at 77 K according to DIN 66131 was 442 m$^2$/g. The total intrusion volume determined according to Hg porosimetry according to DIN 66133 was 4.9 ml/g (milliliter/gram), the respective total pore area 104.6 m$^2$/g. The crystallinity, determined by XRD was 80% and the average crystallite size was 31 nm.

4.5 Impregnation of TiMWW with Zn a) Impregnation

The acid-treated, spray-dried and calcined material as obtained according to 4.4 d) was then subjected to an impregnation stage.

Starting materials: deionized water: 2610.0 kg
    zinc acetate dihydrate: 15.93 kg
    calcined Ti-MWW 4.4.d): 87.0 kg Impregnation was carried out in 3 batches a) to c) as follows:

a) In a vessel equipped with a reflux condenser, a solution of 840 kg deionized water and 5.13 kg zinc acetate dihydrate was prepared within 30 min. Under stirring (40 r.p.m.), 28 kg of the calcined Ti-MWW material obtained according to 4.4.d) were suspended. Subsequently, the vessel was closed and the reflux condenser put into operation. The stirring rate was increased to 70 r.p.m.

b) In a vessel equipped with a reflux condenser, a solution of 840 kg deionized water and 5.13 kg zinc acetate dihydrate was prepared within 30 min. Under stirring (40 r.p.m.), 28 kg of the calcined Ti-MWW material obtained according to 4.4.d) were suspended. Subsequently, the vessel was closed and the reflux condenser put into operation. The stirring rate was increased to 70 r.p.m.

c) In a vessel equipped with a reflux condenser, a solution of 930 kg deionized water and 5.67 kg zinc acetate dihydrate was prepared within 30 min. Under stirring (40 r.p.m.), 31 kg of the calcined Ti-MWW material obtained according to 4.4.d) were suspended. Subsequently, the vessel was closed and the reflux condenser put into operation. The stirring rate was increased to 70 r.p.m.

In all batches a) to c), the mixture in the vessel was heated to 100° C. within 1 h and kept under reflux for 4 h at a stirring rate of 70 r.p.m. Then, the mixture was cooled within 2 h to a temperature of less than 50° C. For each batch a) to c), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h.

For batch a), 106.5 kg nitrogen-dried filter cake were finally obtained. For batch b), 107.0 kg nitrogen-dried filter cake were finally obtained. For batch c), 133.6 kg nitrogen-dried filter cake were finally obtained.

Characterization

The thus dried Zn-impregnated TiMWW material (ZnTi-MWW), for each batch, had a silicon content of 42 weight-%, a titanium content of 1.6 weight-%, a zinc content of 1.4 weight-% and a total organic carbon content of 1.4 weight-%.

b) Spray-Drying the Zn/Ti-MWW Powder

From 347.1 kg of the mixture of the filter cakes obtained from Example 4.5, an aqueous suspension was prepared with deionized water, the suspension having a solid content of 15 weight-%. This suspension was subjected to spray-drying in a spray-tower with the following spray-drying conditions:

apparatus used: spray tower with one nozzle
operation mode: nitrogen straight
configuration: dehumidifier-filter-scrubber
dosage: flexible-tube pump VF 10 (supplier: Verder)
    nozzle with a diameter of 4 mm (supplier: Niro)
filter material: Nomex® needle-felt 10 m$^2$

|  |  | Runtime/h | | | | |
|---|---|---|---|---|---|---|
|  |  | 0.5 | 1.5 | 2.5 | 3.5 | 4.5 |
|  | Flow rate gas/(kg/h) | 550 | 550 | 550 | 550 | 550 |
| Temperature drying gas/° C. | spray tower (in) | 305 | 305 | 305 | 305 | 305 |
|  | spray tower (out) | 151 | 151 | 151 | 151 | 151 |
|  | Filter (in) | 140 | 137 | 130 | 127 | 126 |
|  | Scrubber (in) | 110 | 110 | 110 | 108 | 105 |
|  | Scrubber (out) | 14 | 14 | 15 | 15 | 15 |
| Differential pressure/mbar | spray tower | 3.1 | 3 | 3 | 2.8 | 2.9 |
|  | Filter | 1.7 | 1.7 | 1.8 | 1.8 | 2.1 |
|  | Scrubber | 3.8 | 4.1 | 4.2 | 4.2 | 4.2 |
| Pressure/mbar | spray tower | −103 | −1.2 | −0.9 | −0.9 | −1.1 |
| Nozzle gas | Flow rate kg/h | 23 | 23 | 23 | 23 | 23 |
|  | Temperature/° C. | r.t.*) | r.t.*) | r.t.*) | r.t.*) | r.t.*) |
|  | Pressure/bar | 2.5 | 2.5 | 2.5 | 2.5 | 2.5 |
| Spray-dried product | Temperature/° C. | r.t.*) | r.t.*) | r.t.*) | r.t.*) | r.t.*) |

*)Room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

Characterization

The spray-dried material thus obtained had a zinc content of 1.4 weight-%, a titanium content of 1.7 weight-%, a silicon content of 40 weight-%, and a total organic carbon content of 0.27 weight-% c) Calcination

The spray-dried product was then subjected to calcination for 2 h at 650° C. under air in a rotary furnace, yielding 76.3 kg of calcined spray-dried ZnTi-MWW.

Characterization

The calcined spray-dried material thus obtained had a zinc content of 1.4 weight-%, a titanium content of 1.7 weight-%, a silicon content of 42 weight-%, and a total organic carbon content of 0.14 weight-%.

The bulk density of the calcined spray-dried ZnTi-MWW was 90 g/l (gram/liter). The micropores of the ZnTi-MWW contained in the micropowder had an average pore diameter of 1.13 nm as determined by nitrogen adsorption according to DIN 66134 (Horward-Kawazoe method). The Dv10 value of the particles of the micropowder as determined by Malvern 5.18 micrometers. The Dv50 value of the particles of the micropowder was 24.8 micrometers. The Dv90 value of the particles of the micropowder was 93.53 micrometers. The degree of crystallization determined via XRD was 86%, and the average crystallite size 38.5 nm. The Langmuir surface are determined via nitrogen adsorption at 77 K according to DIN 66134 was 586 m$^2$/g, the BET specific surface area determined via nitrogen adsorption at 77 K according to DIN 66134 was 423 m$^2$/g. The total intrusion volume determined according to Hg porosimetry according to DIN 66133 was 4.3 ml/g (milliliter/gram), the respective total pore area was 80.7 m$^2$/g.

Example 5: Synthesis of a Tin-Containing Zeolitic Material Having an MWW Framework Structure (Sn-MWW)

Example 5.1: Preparation of a B-MWW 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW had a pH of 11.3 as determined via measurement with a pH-sensitive electrode. From said suspension, the B-MWW was separated by filtration. The filter cake was then washed with de-ionized water at room temperature until the washing water had a conductivity of less than 700 microSiemens/cm. The thus obtained filter cake was subjected to spray-drying in a spray-tower with the following spray-drying conditions:

drying gas, nozzle gas: technical nitrogen
temperature drying gas:
    temperature spray tower (in): 235° C.
    temperature spray tower (out): 140° C.
nozzle:
    two-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 m$^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 600° C. for 10 h. The calcined material had a molar ratio $B_2O_3$:$SiO_2$ molar ratio of 0.06:1.

Example 5.2: Deboronation 9 kg of de-ionized water and 600 g of the calcined zeolitic material obtained according to Example 5.1 were refluxed at 100° C. under stirring at 250 r.p.m. for 10 h. The resulting deboronated zeolitic material was separated from the suspension by filtration and washed with 4 l deionized water at room temperature. After the filtration, the filter cake was dried at a temperature of 120° C. for 16 h.

The dried zeolitic material having an MWW framework structure had a $B_2O_3:SiO_2$ molar ratio of 0.0020:1.

Example 5.3: Incorporation of Sn 776.25 g deionized water were provided in a glass beaker and 280 g piperidine were added under stirring and further stirred for 20 minutes. Separately, in a glovebox 5 g tin(IV)-tertbutoxyde were dissolved in 95 g piperidine under nitrogen atmosphere. The mixture was added to the aqueous piperidine suspension and further stirred for 10 minutes. 172.4 g zeolitic material obtained according to Example 5.2 were added to the mixture and stirred for 1 h (200 r.p.m.) at room temperature. The obtained suspension was than filled in an autoclave. The mixture was treated for 120 h at a temperature of 170° C. under stirring (100 r.p.m.).

Afterwards the autoclave was cooled down to room temperature and the resulting zeolitic material was separated from the suspension by filtration at room temperature and washed with deionized water until the washing water had a conductivity of less than 300 microSiemens/cm. After the filtration, the filter cake was dried at a temperature of 120° C. for 16 h.

Characterization

The dried zeolitic material had a silicon content of 37 weight-% and a tin content of 0.68 weight-%.

Example 5.4: Acid Treatment 170 g zeolitic material obtained according to Example 5.3 were provided in a round bottom flask and 5.1 kg of a 30 weight-% $HNO_3$ aqueous solution, having a pH in the range from 0 to 1, were added. The mixture was stirred at a temperature of 100° C. for a period of 20 h (200 r.p.m.). The suspension was filtered and the filter cake was then washed with deionized water at room temperature until the washing water had a pH of approximately 7. The obtained zeolitic material was dried at 120° C. for 16 h and calcined by heating to 550° C. (2° C. per minute) and subsequent heating at 550° C. for 10 h.

Characterization

Figure 2:
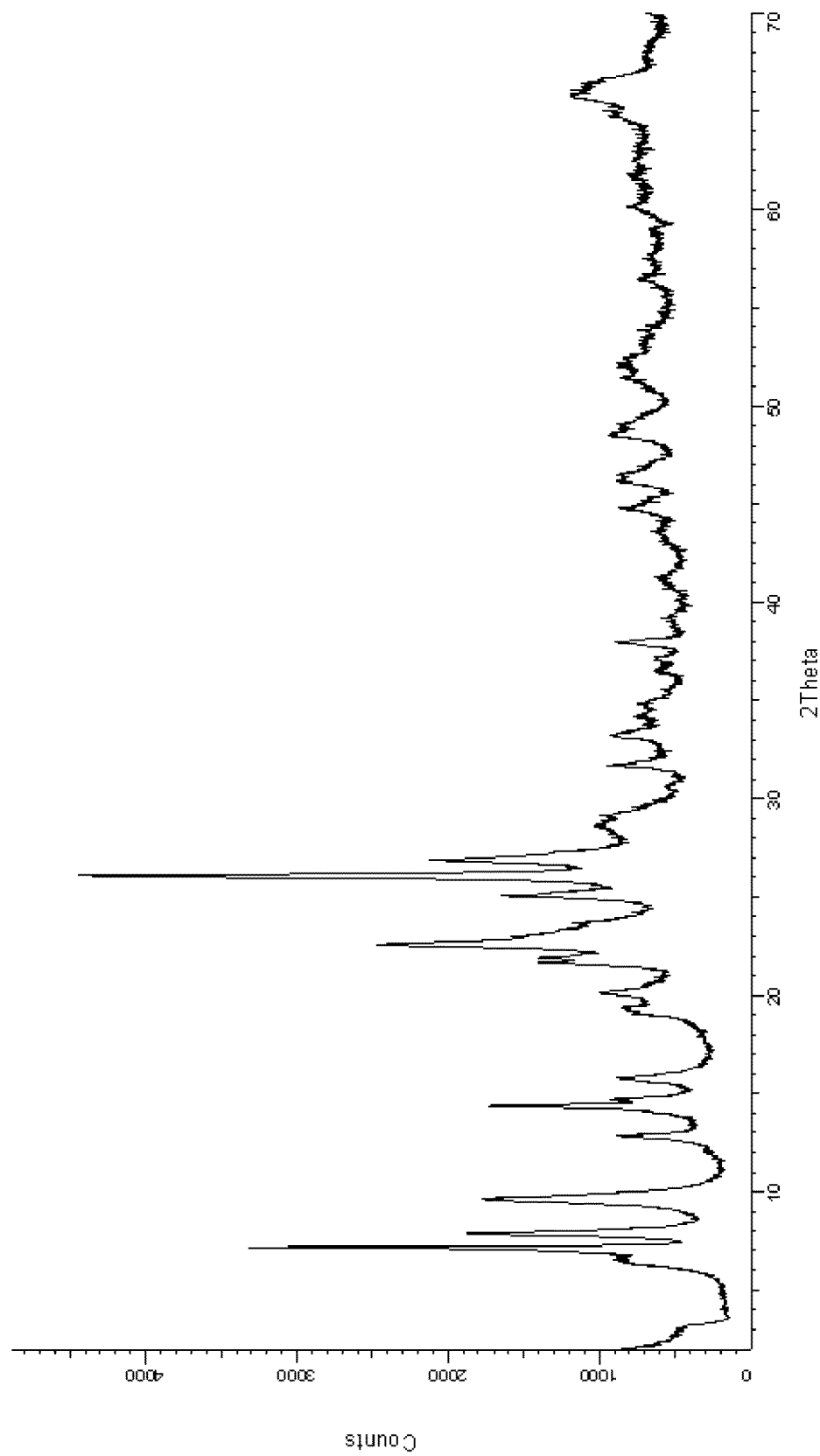
FIG. 2: shows the X-ray diffraction (XRD) pattern (measured using Cu K alpha-1 radiation) of the tin-containing zeolitic material (Sn-MWW) obtained from Example 5. In the figure, the diffraction angle 2 theta in ° is shown along the abscissa and the intensities are plotted along the ordinate

The dried and cacined zeolitic material had a silicon content of 43.5 weight-% and a tin content of 0.78 weight-% and a c parameter as determined via XRD of 27.069 Angstrom. Further, the zeolitic material had a BET surface area, determined according to DIN 66131 of 475 m²/g, a Langmuir surface, determined according to DIN 66135 of 657 m²/g and a total pore area of 189.42 m²/g. The XRD of the obtained zeolitic material is shown in FIG. 2.

Example 6: Synthesis of a Crystalline Zirconium-Containing Silicate (Zr-Silicate)

Example 6.1: Incorporation of Zirconium 540 g of water and 260.64 g of piperidine were introduced in a glass flask. The mixture was stirred at 200 rpm and 24.56 g of Zirconium-n-propoxide were added. The obtained mixture was further stirred for 20 min before drop-wise addition of 180 g of the deboronated zeolitic material having an MWW framework structure obtained according to Example 3.2. The suspension was further stirred for 2 h at 200 rpm until a gel was obtained. The formed gel was transferred to an autoclave. The autoclave was heated to 170° C. and kept at this temperature for 120 h under stirring at 150 rpm. Subsequently, the autoclave was cooled down and the solid was separated by filtration and washed until the washing water had a pH of 7. The filtercake was dried in a static oven at 120° C. for 16 h.

Characterization

Figure 3:
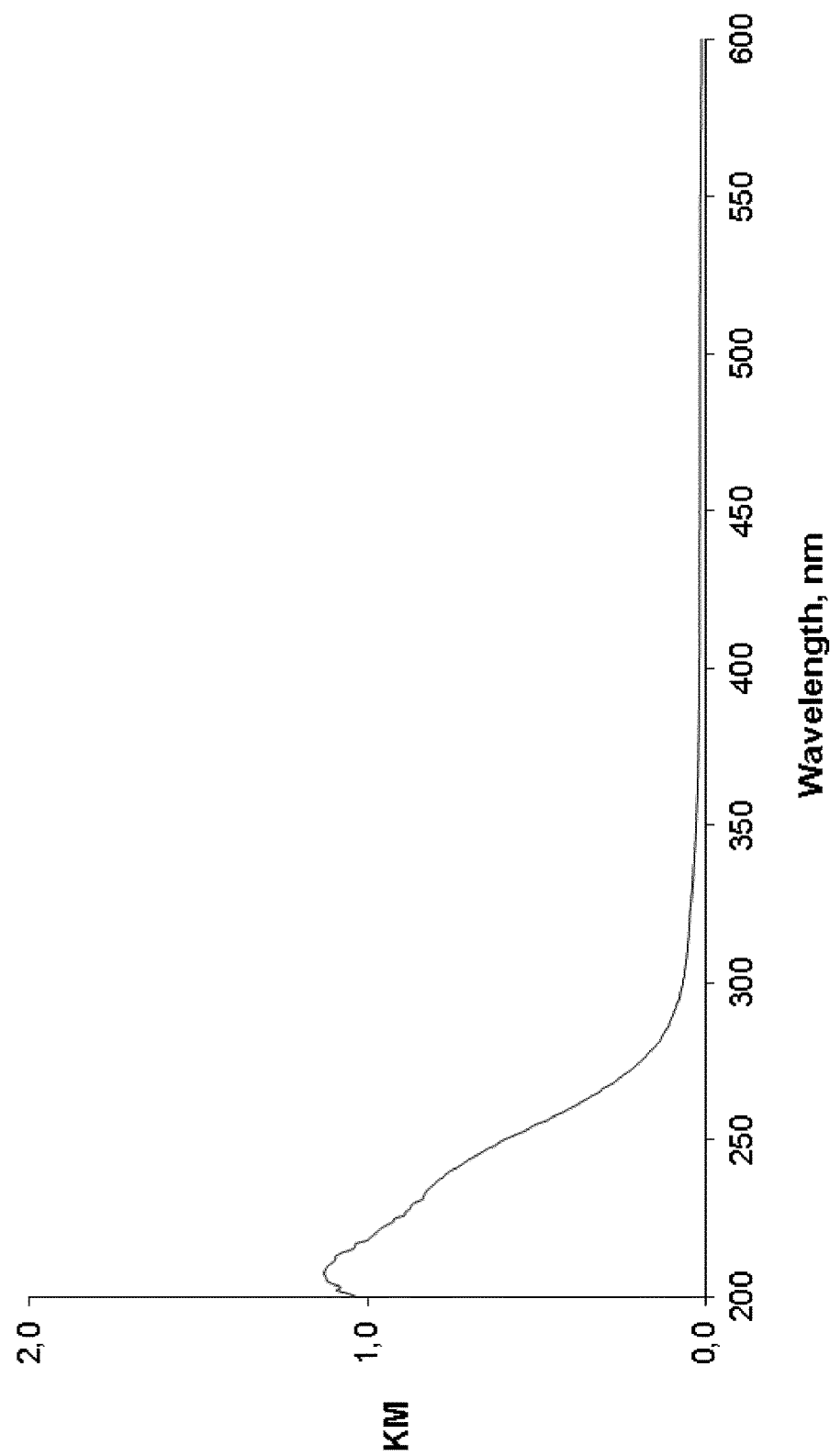
FIG. 3: shows the UV-VIS spectra of Ta-MWW obtained according to Example 8. On the abscissa, the wavelength values (nanometer) are shown, and the Kubelka-Munk "KM" units are plotted along the ordinate.

The obtained zirconium-containing zeolitic material had a zirconium content of 0.73 weight-% and a silicon content of 38.5 weight-%. The XRD of the obtained zeolitic material is shown in FIG. 3.

Example 6.2: Acid Treatment of the Zirconium Containing Zeolitic Material 4200 g of an aqueous $HNO_3$ solution (30 weight-% in water) was provided in a 10 L flask. To this solution the zirconium-containing silicate obtained according to Example 6.1 was added and the mixture was heated to 100° C. for 20 h under stirring with 170 rpm. Afterwards the suspension was filtered and washed until the washing water had a pH of 7. The filtercake was dried in a static oven for 16 h at 120° C. and calcined at 550° C. for 10 h.

Characterization

The obtained zeolitic material had a zirconium content of 0.73 weight-% and a silicon content of 43 weight-%. The BET specific surface area determined via nitrogen adsorption at 77 K according to DIN 66131 was 100 m²/g.

Example 7: Regeneration of the Zr-Silicate

After the conversion of a mixture of ethanol and acetaldehyde according to Example 15, the catalyst was regenerated directly after the reaction inside the reactor. Therefore, the catalyst was heated with a heating ramp of 1 K/min to 500° C. under a 2 vol.-% 02 atmosphere. The temperature was kept at 550° C. for 7 h. Afterwards, the catalyst was cooled to 350° C. and subjected to the conversion of a mixture of ethanol and acetaldehyde according to Example 16.

Example 8: Synthesis of a Crystalline Tantalum-Containing MWW (Ta-MWW)

0.74 g tantalum oxalate-solution (25.7 g Ta/L (delivered from H.C. Starck, specification ID: D3067/02, order-Nr.: 1060010508)) was diluted with 7.4 mL distilled water and added to 5 g deborated MWW obtained from Example 4.2 and the suspension was allowed to stand for 2 h. Thereafter, the suspension was dried at a temperature of 120° C. for 2 h followed by drying at a temperature 500° C. for 4 h, using a heating ramp of 1.5° C./min.

Characterization

The obtained zeolitic material had a tantalum content of 1.5 weight-% and a silicon content of 41 weight-%. The BET specific surface area determined via nitrogen adsorption at 77 K according to DIN 66131 was 436 m²/g.

The material was further characterized by UV-VIS measurements (see FIG. 3). As may be taken from the spectrum in FIG. 3, the maximum of the absorbtion is found in the range of from 205 to 220 nm indicating prevalent tetrahedrally coordinated Ta sites as these are found in the framework of the zeolite structure. Furthermore, no tantalum oxide would appear to be detected in the obtained material since there is no signal above 300 nm. Thus, it is apparent from the US-vis spectrum that the major portion of the tantalum contained in the material is isomorphously substituted in the framework structure. In this respect, reference is made to Catal Lett (2010) 135:169-174 with regard to the characterization of the tantalum sites in a zeolitic material via UV-vis measurements.

The XRD of the obtained zeolitic material is shown in FIG. 5, indicating the material's MWW framework structure.

Example 9: Synthesis of a Crystalline Tantalum-Containing MWW (Ta-MWW)

2.12 g tantalum oxalate-solution (25.7 g Ta/L (delivered from H.C. Starck, specification ID: D3067/02, order-Nr.: 1060010508)) was diluted with 6.2 mL distilled water and added to 5 g deborated MWW obtained from Example 4.2 and the suspension was allowed to stand for 2 h. Thereafter, the suspension was dried at a temperature of 120° C. for 2 h followed by drying at a temperature 500° C. for 4 h, using a heating ramp of 1.5° C./min.

Characterization

Figure 4:
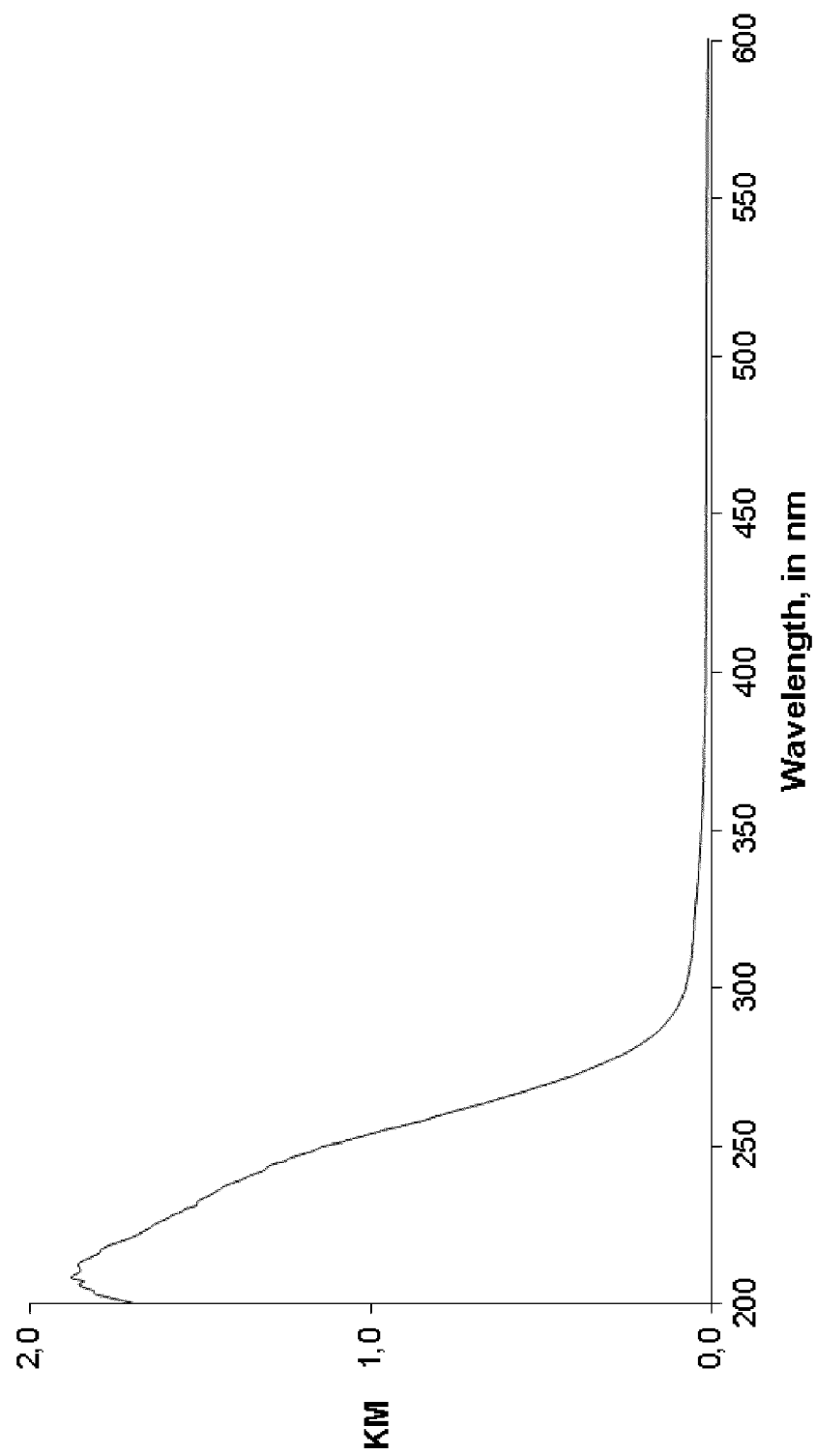
FIG. 4: shows the UV-VIS spectra of Ta-MWW obtained according to Example 9. On the abscissa, the wavelength values (nanometer) are shown, and the Kubelka-Munk "KM" units are plotted along the ordinate.
Figure 5:
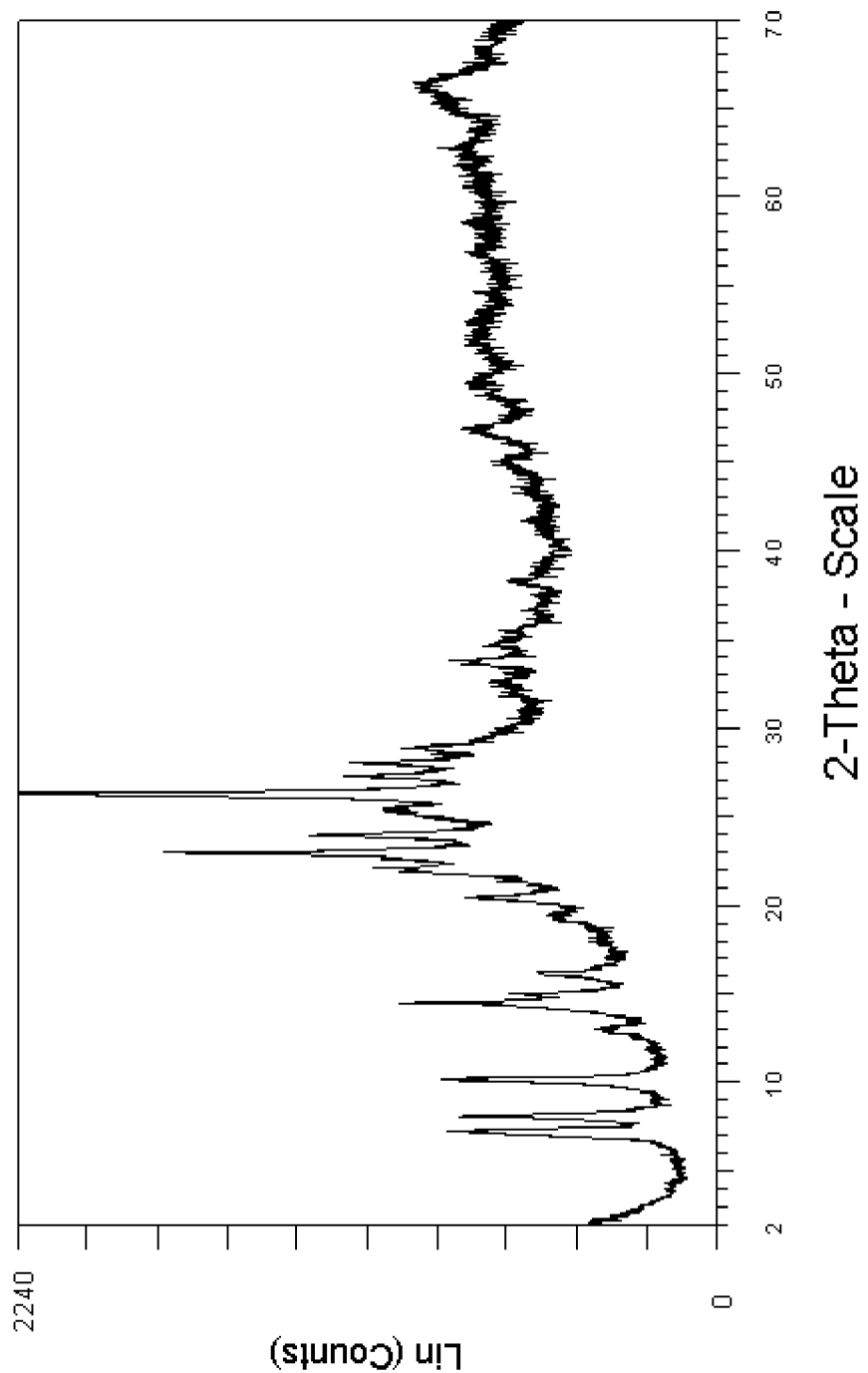
FIG. 5: shows the X-ray diffraction (XRD) pattern (measured using Cu K alpha-1 radiation) of the tantalum-containing zeolitic material (Ta-MWW) obtained from Example 8. In the figure, the diffraction angle 2 theta in ° is shown along the abscissa and the intensities are plotted along the ordinate

The obtained zeolitic material had a tantalum content of 4.9 weight-% and a silicon content of 39 weight-%. The BET specific surface area determined via nitrogen adsorption at 77 K according to DIN 66131 was 416 m$^2$/g. The material was further characterized by UV-VIS measurements (see FIG. 4). As may be taken from the spectrum in FIG. 4, the maximum of the absorbtion is found in the range of from 205 to 220 nm indicating prevalent tetrahedrally coordinated Ta sites as these are found in the framework of the zeolite structure. Furthermore, no tantalum oxide would appear to be detected in the obtained material since there is no signal above 300 nm. Thus, it is apparent from the US-vis spectrum that the major portion of the tantalum contained in the material is isomorphously substituted in the framework structure. In this respect, reference is made to Catal Lett (2010) 135:169-174 with regard to the characterization of the tantalum sites in a zeolitic material via UV-vis measurements.

Comparative Example 1: Synthesis of a Zeolitic Material Having an MWW Framework Structure (Si-MWW)

Comparative Example 1.1: Preparation of Boron-Containing MWW 480 kg de-ionized water were provided in a vessel. Under stirring at 70 r.p.m., 166 kg boric acid were suspended in the water. The suspension was stirred for another 3 h. Subsequently, 278 kg piperidine were added, and the mixture was stirred for another hour. To the resulting solution, 400 kg Ludox® AS-40 were added, and the resulting mixture was stirred at 70 rpm for another hour.

The finally obtained mixture was transferred to a crystallization vessel and heated to 170° C. within 5 h under autogenous pressure and under stirring (50 r.p.m.). The temperature of 170° C. was kept essentially constant for 120 h; during these 120 h, the mixture was stirred at 50 r.p.m. Subsequently, the mixture was cooled to a temperature of from 50-60° C. within 5 h. The aqueous suspension containing B-MWW had a pH of 11.3 as determined via measurement with a pH electrode. After cooling the reactor a solution of 10 weight-% HNO$_3$ was added to the suspension until the suspension had a pH in the range of from 7 to 8.

From said suspension, the B-MWW was separated by filtration. The filter cake was then washed with de-ionized water until the washing water had a conductivity of less than 700 microSiemens/cm From the thus obtained filter cake, an aqueous suspension was prepared with deionized water, the suspension having a solid content of 15 weight-%. This suspension was subjected to spray-drying in a spray-tower with the following spray-drying conditions:

temperature drying gas:
   temperature spray tower (in): 206° C.
   temperature spray tower (out): 120° C.
nozzle:
   two-component nozzle supplier Gerig; size 0
   nozzle gas pressure: 1 bar
apparatus used: spray tower with one nozzle
operation mode: nitrogen straight
configuration: dehumidifier-filter-scrubber
gas flow: 45 kg/h The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 650° C. in a rotary calcined with a throughput of 0.8-1.0 kg/h.

Characterization

The calcined material had a boron content of 1.3 weight-%, a silicon content of 44 weight-%, and a total organic carbon content of <0.1 wt. %. Crystallinity determined by XRD was 88%, BET specific surface area determined via nitrogen adsorption at 77 K according to DIN 66131 was 464 m$^2$/g, pore volume determined by HG porosimetry according to DIN 66133 was 6.3 mL/g, particle size distribution of the sprayed-dried particle determined by Malvern Dv50 was 26.9 μm.

Comparative Example 1.2: Preparation of Deborated MWW 1590 kg water were passed into a vessel equipped with a reflux condenser. Under stirring at 40 r.p.m., 106 kg of the spray-dried material obtained according to section 1.1 were suspended into the water. Subsequently, the vessel was closed and the reflux condenser put into operation. The stirring rate was increased to 70 r.p.m. Under stirring at 70 r.p.m., the content of the vessel was heated to 100° C. in 2 h and kept at this temperature for 10 h. Then, the content of the vessel was cooled to a temperature of less than 50° C.

The resulting deboronated zeolitic material of structure type MWW was separated from the suspension by filtration and washed with 600 L deionized water. After the filtration, the filter cake was sprayed-dried.

Characterization

The dried MWW material obtained had a boron content of 0.04 weight-%, an silicon content of 42 weight-%, and a total organic carbon content of <0.1 wt. %. The BET specific surface area determined via nitrogen adsorption at 77 K according to DIN 66131 was 461 m$^2$/g, the crystallinity, determined by XRD was 82%. The particle size distribution obtained from Malvern measurement was Dv50 11.1 μm.

Conversion of a Mixture of Ethanol and Acetaldehyde in the Presence of a Catalyst The process for the preparation of butadiene by the conversion of a mixture of ethanol and acetaldehyde in the presence of a catalyst according to Reference Example 4 was carried out by use of several catalysts:

Example 10

Was carried out as described in reference Example 4 by use of the Zr-BEA obtained from Example 1, according to the present invention.

Example 11

Was carried out as described in reference Example 4 by use of the Zr-BEA obtained from Example 2, according to the present invention.

Example 12

Figure 6:
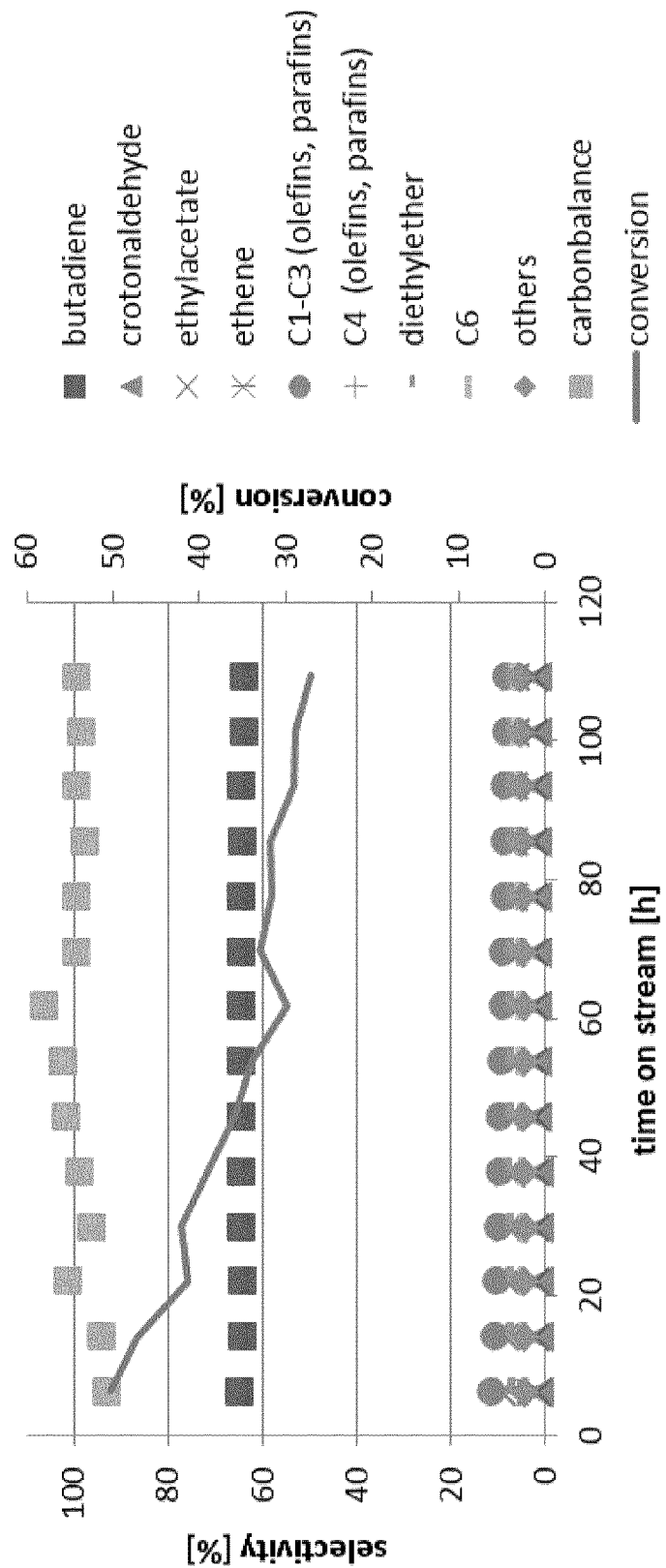
FIG. 6: shows the product formation and ethanol/acetaldehyde conversion as function of time by use of the Zr-silicate obtained from Example 3. On the x axis, the percent values are shown for the conversion of ethanol, as well as for the selectivity relative to ethylene, crotonaldehyde, ethylacetate, ethene, C1 to C3 compounds, C4-compounds, diethylether, C6 compounds, and other compounds, and on the y axis, the time in h is indicated.

Was carried out as described in reference Example 4 by use of the Zr-silicate obtained from Example 3, according to the present invention. The result of this experiment is shown in FIG. 6.

Example 13

Was carried out as described in reference Example 4 by use of the ZnTi-MWW obtained from Example 4, according to the present invention.

Example 14

Was carried out as described in reference Example 4 by use of the Sn-MWW obtained from Example 5, according to the present invention.

Example 15

Was carried out as described in reference Example 4 by use of the Zr-silicate obtained from Example 6, according to the present invention.

Example 16

Was carried out as described in reference Example 4 by use of the Zr-silicate obtained from Example 7, according to the present invention.

Example 17

Was carried out as described in reference Example 4 by use of the Ta-MWW obtained from Example 8, according to the present invention.

Example 18

Was carried out as described in reference Example 4 by use of the Ta-MWW obtained from Example 9, according to the present invention.

Comparative Example 2

Was carried out as described in reference Example 4 by use of the Si-MWW obtained from Comparative Example 1.

Comparative Example 3

Was carried out as described in reference Example 4 by use of $ZrO_2$ (Commercial BASF sample (D9-89)).

The obtained selectivities towards butadiene, ethyl ether and crotonaldehyde are shown in Table 1, wherein the selectivities are calculated based on the total amount of obtained products and given in percentage values.

TABLE 1

Obtained selectivity's of Examples 10 to 16 and Comparative Examples 2 and

| | Experiment | | | | | | |
|---|---|---|---|---|---|---|---|
| | Ex. 10 Zr-BEA | Ex. 11 Zr-BEA | Ex. 12 Zr-silicate | Ex. 13 ZnTi-MWW | Ex. 14 Sn-MWW | Ex. 15 Zr-silicate | Ex. 16 Zr-silicate regener. |
| selectivity to butadiene | 38 | 38 | 64 | 27 | 10 | 64 | 64 |
| selectivity to diethyl ether | 21 | 24 | 8 | 26 | 61 | 5 | 8 |
| selectivity to crotonaldehyde | 2 | 3 | 1 | 8 | 4 | 1 | 1 |
| selectivity to ethylacetate | 3 | 3 | 2 | 8 | 0 | 2 | 3 |
| selectivity to ethene | 11 | 10 | 7 | 17 | 19 | 4 | 4 |
| selectivity to $C_1$ to $C_4$-compounds (olefins/parafins; excluding ethene) | 9 | 6 | 7 | 8 | 2 | 9 | 8 |
| selectivity to $C_6$-compounds | 4 | 3 | 5 | 1 | 1 | 8 | 6 |
| Selectivity to other compounds | 12 | 13 | 5 | 6 | 2 | 6 | 6 |
| Conversion of ethanol/acetaldehyde | 20 | 13 | 36 | 32 | 24 | 47 | 43 |

TABLE 1-continued

Obtained selectivity's of Examples 10 to 16 and Comparative Examples 2 and

|  | Experiment | | | |
| --- | --- | --- | --- | --- |
|  | Ex. 17 Ta-MWW | Ex. 18 Ta-MWW | Comp. Ex. 2 Si-MWW | Comp. Ex. 3 ZrO$_2$ |
| selectivity to butadiene | 72 | 72 | 7 | 13 |
| selectivity to diethyl ether | 4 | 4 | 43 | 6 |
| selectivity to crotonaldehyde | 0 | 1 | 7 | 0 |
| selectivity to ethylacetate | 1 | 1 | 0 | 0 |
| selectivity to ethene | 7 | 7 | 37 | 43 |
| selectivity to C$_1$ to C$_4$-compounds (olefins/parafins; excluding ethene) | 4 | 5 | 2 | 6 |
| selectivity to C$_6$-compounds | 6 | 5 | 0 | 8 |
| Selectivity to other compounds | 6 | 5 | 2 | 20 |
| Conversion of ethanol/acetaldehyde | 39 | 42 | 26 | 93 |

Summary and Comparison of the Results of Examples 10 to 18 and Comparative Examples 2 and 3.

Examples 10 to 18 are carried out according to the present invention, i.e. by a gas-phase process for the preparation of butadiene comprising providing a gas stream comprising ethanol and contacting the gas stream comprising ethanol with a catalyst, wherein the catalyst comprises a zeolitic material having a framework structure comprising one or more tetravalent elements, wherein at least a portion of the one or more tetravalent elements comprised in the framework structure is isomorphously substituted. In Examples 10 to 12 and 15 to 16 the framework structure comprises silicon, wherein a portion of silicon is isomorphously substituted by zirconium. In Example 13 the framework structure comprises silicon, wherein a portion of silicon is isomorphously substituted by titanium and in Example 14 the framework structure comprises silicon, wherein a portion of silicon is isomorphously substituted by tin. Further, in Examples 17 and 18 the framework structure comprises silicon, wherein a portion of silicon is isomorphously substituted by tantalum.

Comparative Examples 2 and 3 are carried out according to a process for the preparation of butadiene comprising contacting a gas stream of ethanol and acetaldehyde with a catalyst comprising silicon (Comparative Example 2) or zirconium (Comparative Example 3), respectively, wherein the tetravalent element comprised in the catalyst is not isomorphously substituted by another element.

In Examples 10, 11, 12, 15 and 16 which are carried out according to the invention by use of a catalyst comprising a zeolitic material having a framework structure comprising zirconium and silicon, unexpectedly high selectivities to butadiene in the range of from 38 to 64% are achieved, wherein the catalysts containing the zirconium-containing silicate (Zr-silicate) affords an astonishingly high selectivity of 64%, wherein at the same time unexpected high conversions of ethanol and acetaldehyde in the range of from 43 to 47% were achieved. Further, Example 13 is carried out according to the invention, wherein a catalyst comprising the ZnTi-MWW is used which leads to a selectivity of 27% to butadiene. Furthermore, in Examples 17 and 18 which are carried out according to the invention by use of a catalyst comprising a zeolitic material having an MWW framework structure comprising tantalum and silicon, unexpectedly high selectivities to butadiene of 72% were achieved and at the same time high conversions of ethanol and acetaldehyde in the range of from 39 to 42% were achieved. Thus, it was surprisingly found that by use of catalysts comprising a zeolitic material according to the present invention, very high selectivities to butadiene and at the same time high conversions of ethanol and acetaldehyde are achieved.

In Example 14, which is carried out according to the invention by use of a catalyst comprising Sn-MWW, and in Comparative Examples 2 and 3, similar selectivities to butadiene are achieved. However, in Example 14 according to the invention, a selectivity to diethyl ether of 61% is achieved, wherein in the Comparative Examples 2 and 3 only a selectivity of 43% and 6%, respectively is achieved. Diethyl ether is a product of the present invention which can be hydrolyzed and recycled into the gas-phase process to obtain butadiene. Therefore, it was found that although the use of the Sn-MWW according to the present invention and the catalysts used in Comparative Examples 2 and 3 lead to similar selectivities to butadiene, the catalyst comprising the Sn-MWW according to the present invention has the advantage that diethyl ether is obtained in a high amount which can be hydrolyzed and recycled into the gas-phase process. Therefore, the use of the catalyst used in Example 14 leads to a far better yield compared to the catalysts used in Comparative Examples 2 and 3.

In Examples 15 and 16 which are carried out according to the invention by use of a catalyst comprising a zeolitic material having a framework structure comprising zirconium and silicon, wherein the catalyst used in Example 15 is regenerated and used in Example 16, selectivities to butadiene of 64% and conversions of the starting material of 47% and 43%, respectively, were achieved. Therefore, it was surprisingly found the catalyst activity and selectivity of the catalyst according to the present invention remains constant after regeneration.

Further, as may be taken from FIG. 6, which displays the results of Example 12, the conversion of ethanol and acetaldehyde as well as the selectivity to butadiene remain constant over the whole tested temporal range. Thus, besides displaying excellent selectivities, it has quite unexpectedly been found that the catalyst is further able to maintain these selectivities with not variation whatsoever over a very prolonged time on stream when considering the results of long term testing displayed in FIG. 6. In particular, it has surprisingly been found that a highly stable process may be provided by the present invention, wherein the product spectrum and the high yield in butadiene shows practically no changes over extended periods of time on stream.

Accordingly, considering the detailed results in the foregoing and their discussion above, it was unexpectedly found that the use of a zeolitic material according to the invention leads to a considerable improvement of the process for the preparation of butadiene.

CITED PRIOR ART

GB 331482
U.S. Pat. No. 2,421,361
WO 2012/015340 A1
Catal. Sci. Technol. 1 (2011), 267-272
Ind. Eng. Chem. 41 (1949), pages 1012-1017

The invention claimed is:

1. A gas-phase process for the preparation of butadiene comprising:
   (i) providing a gas stream G-1 comprising ethanol; and
   (ii) contacting the gas stream G-1 comprising ethanol with a catalyst, thereby obtaining a gas stream G-2 comprising butadiene,
   wherein the catalyst comprises a zeolitic material having a MWW framework structure comprising $YO_2$, and
   wherein at least a portion of Y comprised in the framework structure is isomorphously substituted by one or more elements X,
   wherein Y is selected from the group consisting of Si, Sn, Ti, Zr, Ge, and combinations of two or more thereof, and
   wherein X is selected from the group consisting of Zr, Ti, Sn, Ga, Nb, Ta, Sc, Ge, Al, B, Fe, and combinations of two or more thereof.

2. The process of claim 1, wherein the gas stream G-1 additionally comprises acetaldehyde.

3. The process of claim 2, wherein the molar ratio of ethanol to acetaldehyde in the gas stream G-1 is in the range of from 1:1 to 6:1.

4. The process of claim 2, wherein 80 vol.-% or more of the gas stream G-1 comprises ethanol or a mixture of ethanol and acetaldehyde.

5. The process of claim 1, wherein the molar ratio of Y:X in the framework structure ranges from 10:1 to 150:1.

6. The process of claim 1, wherein the molar ratio of Y:X in the framework structure ranges from 50:1 to 700:1.

7. The process of claim 1, wherein the catalyst comprises Sn-MWW and/or Ta-MWW.

8. The process of claim 1, wherein the zeolitic material comprised in the catalyst has an MWW framework structure, and wherein Y is Si and X is Ti.

9. The process of claim 8, wherein the zeolitic material further comprises Zn as a non-framework element.

10. The process of claim 1, wherein the catalyst comprises a zeolitic material having an X-ray powder diffraction pattern comprising at least the following reflections:

| Intensity (%) | Diffraction angle 2θ/° [Cu K(alpha 1)] |
|---|---|
| 67.0-87.0 | 15.16 ± 0.3 |
| 79.8-99.8 | 15.82 ± 0.3 |
| 45.3-65.3 | 22.47 ± 0.3 |
| 100 | 23.88 ± 0.3 |
| 52.3-72.3 | 27.06 ± 0.3 |
| 75.0-95.0 | 27.21 ± 0.3 | wherein 100% relates to the intensity of the maximum peak in the X-ray powder diffraction pattern.

11. The process of claim 1, wherein contacting the gas stream G-1 with the catalyst is carried out at a temperature in the range of from 300 to 500° C.

12. The process of claim 1, wherein contacting the gas stream G-1 with the catalyst is carried out at a pressure in the range of from 1 to 5 bar.

13. The process of claim 1, wherein contacting gas stream G-1 with the catalyst is carried out in a continuous mode.

14. The process of claim 1, wherein contacting the gas stream G-1 with the catalyst is carried out in one or more reactors, and wherein the one or more reactors comprise the catalyst in the form of a fixed bed.

15. The process of claim 1, wherein prior to contacting the gas stream G-1 with the catalyst, the gas stream G-1 is heated.

16. The process of claim 1, wherein prior to contacting the gas stream G-1 with the catalyst, the catalyst is activated.

17. The process of claim 16, wherein the catalyst is activated by heating to a temperature in the range of from 300 to 450° C.

18. The process of claim 16, wherein the catalyst is heated with a temperature ramp in the range of from 0.5 to 10 K/min.

19. The process of claim 16, wherein the catalyst is activated in one or more reactors.

20. The process of claim 16, wherein during heating the catalyst is flushed with an inert gas.

21. The process of claim 1, wherein the gas stream G-2 comprises the butadiene in an amount of from 10 to 90 vol-%, based on the total volume of the gas stream G-2.

22. The process of claim 1, further comprising
   (iii) separating butadiene from the gas stream G-2, thereby obtaining a purified gas stream G-3 comprising butadiene.

23. The process of claim 1, wherein the gas stream G-2 further comprises diethyl ether, and wherein the diethyl ether is separated from the gas stream G-2 to be recycled in the gas-phase process for the preparation of butadiene.

24. The process of claim 23, wherein the gas stream G-2 comprises the diethyl ether in an amount of from 1 to 65 vol-% based on the total volume of the gas stream G-2.

25. The process of claim 23, further comprising hydrolyzing at least a portion of separated diethyl ether to ethanol prior to its recycling to the gas-phase process for the preparation of butadiene.

26. The process of claim 25, wherein the separated diethyl ether is hydrolyzed under acidic conditions.

27. The process of claim 1, wherein the gas stream G-2 further comprises crotonaldehyde.

28. The process of claim 27, wherein the gas stream G-2 comprises the crotonaldehyde in an amount of from 0.1 to 15 vol-%, based on the total volume of the gas stream G-2.

29. The process of claim 1, further comprising regenerating the catalyst.

30. The method of claim 1, wherein a selectivity of the process relative to butadiene is at least 10%.

* * * * *